United States Patent [19]
Chizzonite et al.

[11] Patent Number: 6,046,012
[45] Date of Patent: Apr. 4, 2000

[54] ANTIBODY TO IL-12 RECEPTOR

[75] Inventors: Richard Anthony Chizzonite, South Kent, Conn.; Theresa Patricia Truitt, Bloomfield, N.J.

[73] Assignee: Hoffmann-La Roche Inc., Nutley, N.J.

[21] Appl. No.: 08/789,350

[22] Filed: Jan. 27, 1997

Related U.S. Application Data

[63] Continuation of application No. 08/248,531, May 31, 1994, abandoned, which is a continuation-in-part of application No. 08/094,649, Jul. 19, 1993, abandoned.

[51] Int. Cl.[7] ........................ G01N 33/567; G01N 33/53; G01N 33/566; C07K 16/00
[52] U.S. Cl. ........................ 435/7.21; 435/7.24; 435/971; 435/973; 435/7.94; 435/7.95; 530/389.6; 530/388.77; 436/518; 436/531; 436/534; 436/57; 436/824; 436/501
[58] Field of Search ........................... 435/7.1, 7.2, 7.21, 435/7.24, 7.94, 7.95, 971, 973; 436/518, 531, 534, 57, 172, 824, 501; 530/386.73, 389.6, 388.22, 387.7, 389.1

[56] References Cited

U.S. PATENT DOCUMENTS

| | | |
|---|---|---|
| 4,578,335 | 3/1986 | Urdal et al. . |
| 4,707,443 | 11/1987 | Nelson et al. . |
| 5,225,539 | 7/1993 | Winter . |
| 5,852,176 | 12/1998 | Gubler et al. ........................ 530/389.2 |

FOREIGN PATENT DOCUMENTS

| | | |
|---|---|---|
| 239 400 | 3/1987 | European Pat. Off. . |
| 92/11018 | 7/1992 | WIPO . |

OTHER PUBLICATIONS

Derwent Abstract No. 87–272811/39, (1987).
Derwent Abstract No. 92–249842/30, (1992).
Bird, et al., *Science*, 242:423–426 (1988).
Chizzonite, et al., *J. Immunol.*, 147:1548 (1991).
Chizzonite, et al., *J. Immunol.*, 148:3117 (1992).
Chizzonite, et al., *J. Cell. Biol.*, 17:73 (1993).
Chua, et al., *J. Immunol.*, 153:128–136 (1994).
Desai, et al., *J. Immunol.*, 148:3125 (1992).
Desai, et al., *J. Immunol.*, 150(8):270A (1993).
Gubler, et al., *Proc. Natl. Acad. Sci. USA*, 88:4143–4147 (1991).
Huston, et al., *Proc. Natl. Acad. Sci. USA*, 85:5879–5883 (1988).
King, *J. Immunol. Meth.*, 72:481–488 (1984).
Stern, et al., *Proc. Natl. Acad. Sci. USA*, 87:6808–6812 (1990).
Wolf, et al., *J. Immunol.*, 146:3074–3081 (1991).

*Primary Examiner*—Keith D. MacMillan
*Assistant Examiner*—Joseph W. Ricigliano
*Attorney, Agent, or Firm*—George W. Johnston; William H. Epstein; Briana C. Buchholz

[57] ABSTRACT

This disclosure relates to novel antibodies specific to the recently discovered receptor to human interleukin 12 (IL-12R). The antibodies to IL-12R, most preferably, the monoclonal antibodies to that protein, are useful in determining the status of the human immune system and as diagnostic reagents or potential therapeutic reagents for conditions involving imbalances in IL-12 levels or cell types sensitive to IL-12 activation.

Further aspects of the disclosure relate to methods of producing and purifying such novel antibodies and hybridoma cell lines capable of their production. Another aspect of the disclosure relates to an immunoprecipation assay for the detection of solubilized IL-12R which employs, in a preferred embodiment, monoclonal antibodies to the receptor of the present invention covalently bound to Protein G-Sepharose resin.

17 Claims, 12 Drawing Sheets

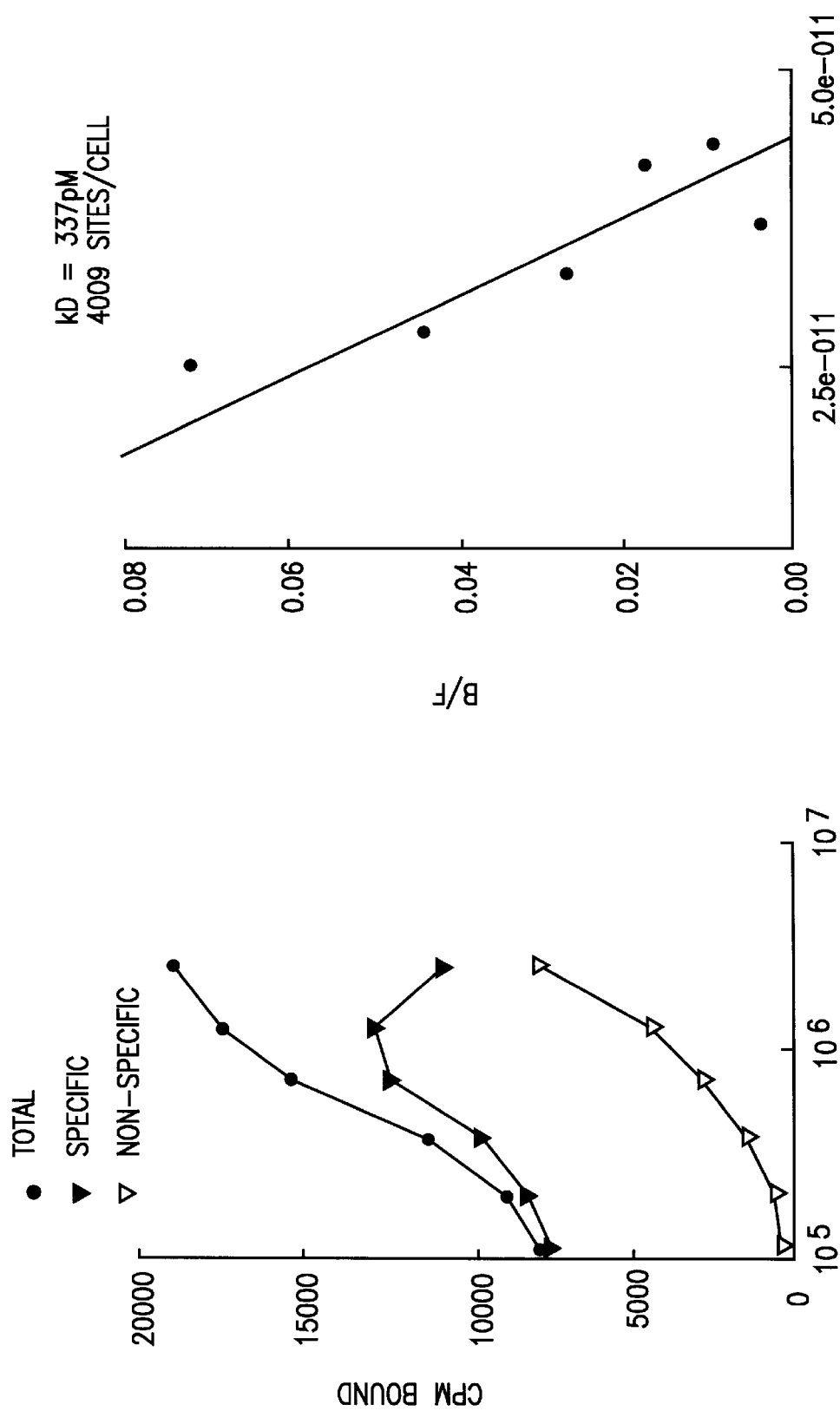

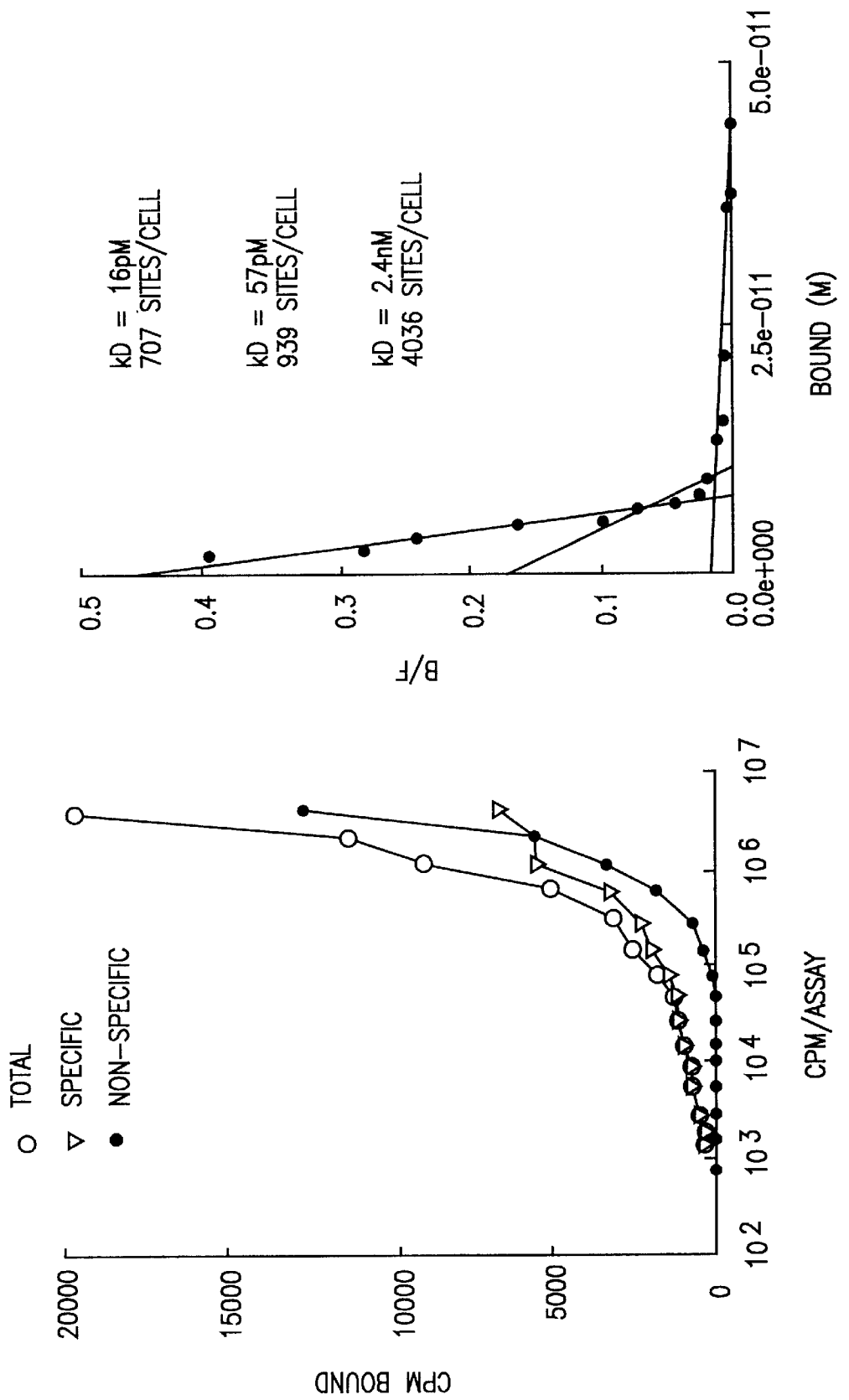

SEQUENCE LISTING

<160> NUMBER OF SEQ ID NOS: 2

<210> SEQ ID NO 1
<211> LENGTH: 2104
<212> TYPE: DNA
<213> ORGANISM: Homo sapiens
<220> FEATURE:
<221> NAME/KEY: misc_feature
<222> LOCATION: (65)..(2050)
<223> OTHER INFORMATION: Protein coding region from 65 through 2050

<400> SEQUENCE: 1

```
ggtggctgaa cctcgcaggt ggcagagagg ctcccctggg gctgtggggc tctacgtgga        60
tccgatggag ccgctggtga cctgggtggt cccccctcctc ttcctcttcc tgctgtccag      120
gcagggcgct gcctgcagaa ccagtgagtg ctgttttcag gaccgccat atccggatgc        180 agactcaggc tcggcctcgg gccctaggga cctgagatgc tatcggatat ccagtgatcg      240
ttacgagtgc tcctggcagt atgagggtcc cacagctggg gtcagccact tcctgcggtg        300
ttgccttagc tccgggcgct gctgctactt cgccgccggc tcagccacca ggctgcagtt      360
```

-continued

```
ctccgaccag gctgggtgt ctgtgctgta cactgtcaca ctctgggtgg aatcctgggc      420
caggaaccag acagagaagt ctcctgaggt gaccctgcag ctctacaact cagttaaata      480
tgagcctcct ctgggagaca tcaaggtgtc caagttggcc gggcagctgc gtatggagtg      540
ggagaccccg gataaccagg ttggtgctga ggtgcagttc cggcaccgga cacccagcag      600
cccatggaag ttgggcgact gcggacctca ggatgatgat actgagtcct gcctctgccc      660
cctggagatg aatgtggccc aggaattcca gctccgacga cggcagctgg ggagccaagg      720
aagttcctgg agcaagtgga gcagcccccgt gtgcgttccc cctgaaaacc ccccacagcc      780
tcaggtgaga ttctcggtgg agcagctggg ccaggatggg aggaggcggc tgaccctgaa      840
agagcagcca acccagctgg agcttccaga aggctgtcaa gggctggcgc ctggcacgga      900
ggtcacttac cgactacagc tccacatgct gtcctgcccg tgtaaggcca aggccaccag      960
gaccctgcac ctggggaaga tgccctatct ctcgggtgct gcctacaacg tggctgtcat     1020
ctcctcgaac caatttggtc ctggcctgaa ccagacgtgg cacattcctg ccgacaccca     1080
cacagaacca gtggctctga atatcagcgt cggaaccaac gggaccacca tgtattggcc     1140
agcccgggct cagagcatga cgtattgcat tgaatggcag cctgtgggcc aggacggggg     1200
ccttgccacc tgcagcctga ctgcgccgca agacccggat ccggctggaa tggcaaccta     1260
cagctggagt cgagagtctg ggcaatgggg gcaggaaaag tgttactaca ttaccatctt     1320
tgcctctgcg caccccgaga agctcacctt gtggtctacg gtcctgtcca cctaccactt     1380
tgggggcaat gcctcagcag ctgggacacc gcaccacgtc tcggtgaaga atcatagctt     1440
ggactctgtg tctgtggact gggcaccatc cctgctgagc acctgtcccg gcgtcctaaa     1500
ggagtatgtt gtccgctgcc gagatgaaga cagcaaacag gtgtcagagc atcccgtgca     1560
gcccacagag acccaagtta ccctcagtgg cctgcgggct ggtgtagcct acacggtgca     1620
ggtgcgagca gacacagcgt ggctgagggg tgtctggagc cagccccagc gcttcagcat     1680
cgaagtgcag gtttctgatt ggctcatctt cttcgcctcc ctggggagct tcctgagcat     1740
ccttctcgtg ggcgtccttg gctaccttgg cctgaacagg gccgcacggc acctgtgccc     1800
gccgctgccc acaccctgtg ccagctccgc cattgagttc cctggaggga aggagacttg     1860
gcagtggatc aacccagtgg acttccagga agaggcatcc ctgcaggagg ccctggtggt     1920
agagatgtcc tgggacaaag gcgagaggac tgagcctctc gagaagacag agctacctga     1980
gggtgcccct gagctggccc tggatacaga gttgtccttg gaggatggag acaggtgcaa     2040
ggccaagatg tgatcgttga ggctcagaga gggtgagtga ctcgcccgag gctacgtagc     2100
cttt                                                                  2104
```

<210> SEQ ID NO 2
<211> LENGTH: 662
<212> TYPE: PRT
<213> ORGANISM: Homo sapiens
<220> FEATURE:
<221> NAME/KEY: SITE
<222> LOCATION: (1)..(23)
<223> OTHER INFORMATION: N-terminal signal peptide (1...20 or 23 or 24)
<220> FEATURE:
<221> NAME/KEY: SITE
<222> LOCATION: (541)..(570)
<223> OTHER INFORMATION: transmembrane region
<220> FEATURE:
<221> NAME/KEY: SITE
<222> LOCATION: (571)..(662)
<223> OTHER INFORMATION: cytoplasmic tail region
<220> FEATURE:

-continued

```
<221> NAME/KEY: SITE
<222> LOCATION: (52)..(64)
<223> OTHER INFORMATION: sequence motif of cytokine receptor superfamily
      CYs52...CYs62SW
<220> FEATURE:
<221> NAME/KEY: SITE
<222> LOCATION: (222)..(226)
<223> OTHER INFORMATION: cytokine receptor superfamily motif (W222SKWS)
<220> FEATURE:
<221> NAME/KEY: SITE
<222> LOCATION: (121)..(123)
<223> OTHER INFORMATION: N-linked glycosylation site
<220> FEATURE:
<221> NAME/KEY: SITE
<222> LOCATION: (329)..(331)
<223> OTHER INFORMATION: N-linked glycosylation site
<220> FEATURE:
<221> NAME/KEY: SITE
<222> LOCATION: (346)..(348)
<223> OTHER INFORMATION: N-linked glycosylation site
<220> FEATURE:
<221> NAME/KEY: SITE
<222> LOCATION: (352)..(354)
<223> OTHER INFORMATION: N-liked glycosylation site
<220> FEATURE:
<221> NAME/KEY: SITE
<222> LOCATION: (442)..(444)
<223> OTHER INFORMATION: N-linked glycosylation site
<220> FEATURE:
<221> NAME/KEY: SITE
<222> LOCATION: (456)..(458)
<223> OTHER INFORMATION: N-linked glycosylation site
<220> FEATURE:
<221> NAME/KEY: SITE
<222> LOCATION: (24)..(540)
<223> OTHER INFORMATION: Extracellular region

<400> SEQUENCE: 2

Met Glu Pro Leu Val Thr Trp Val Val Pro Leu Leu Phe Leu Phe Leu
 1               5                  10                  15

Leu Ser Arg Gln Gly Ala Ala Cys Arg Thr Ser Glu Cys Cys Phe Gln
            20                  25                  30

Asp Pro Pro Tyr Pro Asp Ala Asp Ser Gly Ser Ala Ser Gly Pro Arg
        35                  40                  45

Asp Leu Arg Cys Tyr Arg Ile Ser Ser Asp Arg Tyr Glu Cys Ser Trp
    50                  55                  60

Gln Tyr Glu Gly Pro Thr Ala Gly Val Ser His Phe Leu Arg Cys Cys
65                  70                  75                  80

Leu Ser Ser Gly Arg Cys Cys Tyr Phe Ala Ala Gly Ser Ala Thr Arg
                85                  90                  95

Leu Gln Phe Ser Asp Gln Ala Gly Val Ser Val Leu Tyr Thr Val Thr
            100                 105                 110

Leu Trp Val Glu Ser Trp Ala Arg Asn Gln Thr Glu Lys Ser Pro Glu
        115                 120                 125

Val Thr Leu Gln Leu Tyr Asn Ser Val Lys Tyr Glu Pro Pro Leu Gly
    130                 135                 140

Asp Ile Lys Val Ser Lys Leu Ala Gly Gln Leu Arg Met Glu Trp Glu
145                 150                 155                 160

Thr Pro Asp Asn Gln Val Gly Ala Glu Val Gln Phe Arg His Arg Thr
                165                 170                 175

Pro Ser Ser Pro Trp Lys Leu Gly Asp Cys Gly Pro Gln Asp Asp Asp
            180                 185                 190

Thr Glu Ser Cys Leu Cys Pro Leu Glu Met Asn Val Ala Gln Glu Phe
        195                 200                 205

Gln Leu Arg Arg Arg Gln Leu Gly Ser Gln Gly Ser Ser Trp Ser Lys
```

-continued

```
                210                 215                 220
Trp Ser Ser Pro Val Cys Val Pro Glu Asn Pro Pro Gln Pro Gln
225                 230                 235                 240

Val Arg Phe Ser Val Glu Gln Leu Gly Gln Asp Gly Arg Arg Leu
                245                 250                 255

Thr Leu Lys Glu Gln Pro Thr Gln Leu Glu Leu Pro Glu Gly Cys Gln
                260                 265                 270

Gly Leu Ala Pro Gly Thr Glu Val Thr Tyr Arg Leu Gln Leu His Met
                275                 280                 285

Leu Ser Cys Pro Cys Lys Ala Lys Ala Thr Arg Thr Leu His Leu Gly
    290                 295                 300

Lys Met Pro Tyr Leu Ser Gly Ala Ala Tyr Asn Val Ala Val Ile Ser
305                 310                 315                 320

Ser Asn Gln Phe Gly Pro Gly Leu Asn Gln Thr Trp His Ile Pro Ala
                325                 330                 335

Asp Thr His Thr Glu Pro Val Ala Leu Asn Ile Ser Val Gly Thr Asn
                340                 345                 350

Gly Thr Thr Met Tyr Trp Pro Ala Arg Ala Gln Ser Met Thr Tyr Cys
                355                 360                 365

Ile Glu Trp Gln Pro Val Gly Gln Asp Gly Gly Leu Ala Thr Cys Ser
370                 375                 380

Leu Thr Ala Pro Gln Asp Pro Asp Pro Ala Gly Met Ala Thr Tyr Ser
385                 390                 395                 400

Trp Ser Arg Glu Ser Gly Ala Met Gly Gln Glu Lys Cys Tyr Tyr Ile
                405                 410                 415

Thr Ile Phe Ala Ser Ala His Pro Glu Lys Leu Thr Leu Trp Ser Thr
                420                 425                 430

Val Leu Ser Thr Tyr His Phe Gly Gly Asn Ala Ser Ala Ala Gly Thr
                435                 440                 445

Pro His His Val Ser Val Lys Asn His Ser Leu Asp Ser Val Ser Val
    450                 455                 460

Asp Trp Ala Pro Ser Leu Leu Ser Thr Cys Pro Gly Val Leu Lys Glu
465                 470                 475                 480

Tyr Val Val Arg Cys Arg Asp Glu Asp Ser Lys Gln Val Ser Glu His
                485                 490                 495

Pro Val Gln Pro Thr Glu Thr Gln Val Thr Leu Ser Gly Leu Arg Ala
                500                 505                 510

Gly Val Ala Tyr Thr Val Gln Val Arg Ala Asp Thr Ala Trp Leu Arg
                515                 520                 525

Gly Val Trp Ser Gln Pro Gln Arg Phe Ser Ile Glu Val Gln Val Ser
                530                 535                 540

Asp Trp Leu Ile Phe Phe Ala Ser Leu Gly Ser Phe Leu Ser Ile Leu
545                 550                 555                 560

Leu Val Gly Val Leu Gly Tyr Leu Gly Leu Asn Arg Ala Ala Arg His
                565                 570                 575

Leu Cys Pro Pro Leu Pro Thr Pro Cys Ala Ser Ser Ala Ile Glu Phe
                580                 585                 590

Pro Gly Gly Lys Glu Thr Trp Gln Trp Ile Asn Pro Val Asp Phe Gln
                595                 600                 605

Glu Glu Ala Ser Leu Gln Glu Ala Leu Val Val Glu Met Ser Trp Asp
                610                 615                 620

Lys Gly Glu Arg Thr Glu Pro Leu Glu Lys Thr Glu Leu Pro Glu Gly
625                 630                 635                 640
```

```
-continued

Ala Pro Glu Leu Ala Leu Asp Thr Glu Leu Ser Leu Glu Asp Gly Asp
            645                 650                 655

Arg Cys Lys Ala Lys Met
            660
```

ANTIBODY TO IL-12 RECEPTOR

This application is a continuation of Ser. No. 08/248,531 filed May 31, 1994, now abandoned, which is a continuation in part of application Ser. No. 08/094,649, filed Jul. 19, 1993, now abandoned.

BACKGROUND OF THE INVENTION

IL-12, formerly known as cytotoxic lymphocyte maturation factor, is a cytokine that stimulates proliferation of PHA-activated human peripheral blood lymphoblasts and synergizes with low concentrations of IL-2 in the induction of lymphokine-activated killer cells. IL-12 is a 75-kDa heterodimer composed of disulfide-bonded 40-kDa and 35-kDa subunits. Monoclonal antibodies have been prepared against a partially purified preparation of natural IL-12. These antibodies have been characterized by (1) immunoprecipitation of $^{125}$I-labeled IL-12, (2) immunodepletion of IL-12 bioactivity, (3) Western blotting of IL-12, (4) inhibition of $^{125}$IL-12 binding to its cellular receptor, and (5) neutralization of IL-12 bioactivity. It was determined that antibodies specific for the 40-kDa subunit of IL-12 block receptor binding of $^{125}$IL-12 and neutralize IL-12 activity. See in this regard Chizzonite et al., *J. Immunol.* 147:1548 (1991).

The initial characterization of the IL-12 receptor (IL-12R) has been reported for mitogen- and IL-2-activated human peripheral blood mononuclear cells (PBMC) and tonsilar lymphocytes. Radiolabeled IL-12 binding assays demonstrated that at the time of peak expression, mitogenor IL-2-activated cells expressed 1000 to 9000 IL-12 binding sites/cell with a $K_D$ of approximately 100 to 600 pM. The varations in $K_D$ and sites per cell were dependent on the individual preparations of lymphoblasts. The binding of $^{125}$I-labeled IL-12 to PHA-activate PBMC was saturable and specific, since the binding of radiolabeled ligand was only inhibited by IL-12 and not by other cytokines. Kinetic studies revealed that maximum expression of IL-12R occurred earlier on PHA-activated PBMC as compared with PBMC activated by IL-2, and that expression of IL-12R on these cells correlated with their ability to proliferate in response to IL-2. See Chizzonite et al., *J.Immunol.* 148:3117 (1992) and Desai et al., *J. Immunol.* 148:3125 (1992). Summing the results obtained in these two papers, activation of T cells or NK cells results in up-regulation of IL-12R expression; on the other hand, B cell activation, at least under some circumstances, appears not to be associated with enhanced expression of IL-12R.

SUMMARY OF THE INVENTION

The present invention relates to novel antibodies against the IL-12R. Representative anti-IL-12R antisera provided in accordance with the present invention block IL-12 binding to cells expressing IL-12R and can also neutralize IL-12 activity. In further embodiments of the present invention, monoclonal antibodies which are selective to IL-12R are prepared in accordance with generally known techniques, such as the method of Kohler and Milstein. Suitable monoclonal antibodies to IL-12R can be modified by known methods to provide chimeric, humanized or single chain antibody (SCA) embodiments.

The IL-12R antibodies of the present invention can be used to determine IL-12 receptor expression on human cells, such as peripheral blood lymphocytes and bone marrow cells, in normal and pathological conditions. The antisera and monoclonal antibodies of the invention can also be used to block IL-12 binding to its receptor and thus block its biologic activity. Neutralizing antibodies of the present invention can thus be used for therapeutic intervention in a number of disease states that are aggravated by activated T-cells and NK cells, such as autoimmune diseases, graft versus host disease and rheumatoid arthritis. Finally, as has been specifically demonstrated by the monoclonal antibody embodiment of the present invention, such antibody will also be useful for expression cloning strategies to isolate a cDNA coding for the IL-12 receptor.

BRIEF DESCRIPTION OF THE FIGURES

FIG. 4A shows lymphoblasts (1×10$^6$ cells) were incubated for 2 hrs at room temperature with increasing concentrations of $^{125}$I-2*4E6 in the absence (○) or presence (●) of 25 nM unlabeled 2*4E6. Total (○) and non-specific (●) cell bound radioactivity were determined as described in "Methods". Specific binding of $^{125}$I-2*4E6 (▽) was calculated by subtracting non-specific binding from total binding. FIG. 4B shows analysis of the binding data according to the method of Scatchard as determined by Ligand computer program with a single-site model.

FIGS. 5A and 5B—Equilibrium Binding of $^{125}$I-2*4E6 to Human K6 Cells at Room Temperature FIG. 5A shows K6 cells (1×10$^6$ cells) were inculcated for 2 hrs at room temperature with increasing concentrations of $^{125}$I-2*4E6 in the absence (●) or presence (▽) of 25 nM unlabeled 2*4E6. Total (●) and non-specific (▽) cell bound radioactivity were determined as described in "Methods". Specific binding of $^{125}$I-2*4E6 (▼) was calculated by subtracting non-specific binding from total binding. FIG. 5B shows analysis of the biding data according to the method of Scatchard as determined by Ligand with a single-site model.

The data are expressed as the amount of $^{125}$I-2*4E6 bound [CPM BOUND (Percent)] to the cells in the presence of the indicated concentrations of unlabeled antibody or IL-12 when compared with the total specific binding in the absence of unlabeled competitor.

FIGS. 7A and 7B—Equilibrium Binding of $^{125}$I-IL-12 to Human K6 Cells at Room Temperature FIG. 7A shows K6 cells (1×10$^6$ cells) were incubated for 2 hrs at room temperature with increasing concentrations of $^{125}$I-IL-12 in the absence (○) or presence (●) of 50 nM unlabeled IL-12. Total (○) and non-specific (●) cell bound radioactivity were determined as described in Materials and Methods. Specific binding of $^{25}$I-IL-12 (▽) was calculated by subtracting non-specific binding from total bindings. FIG. 7B shows analysis of the binding data according to the method of Scatchard as determined by Ligand with a single-site model.

Figure 8B:
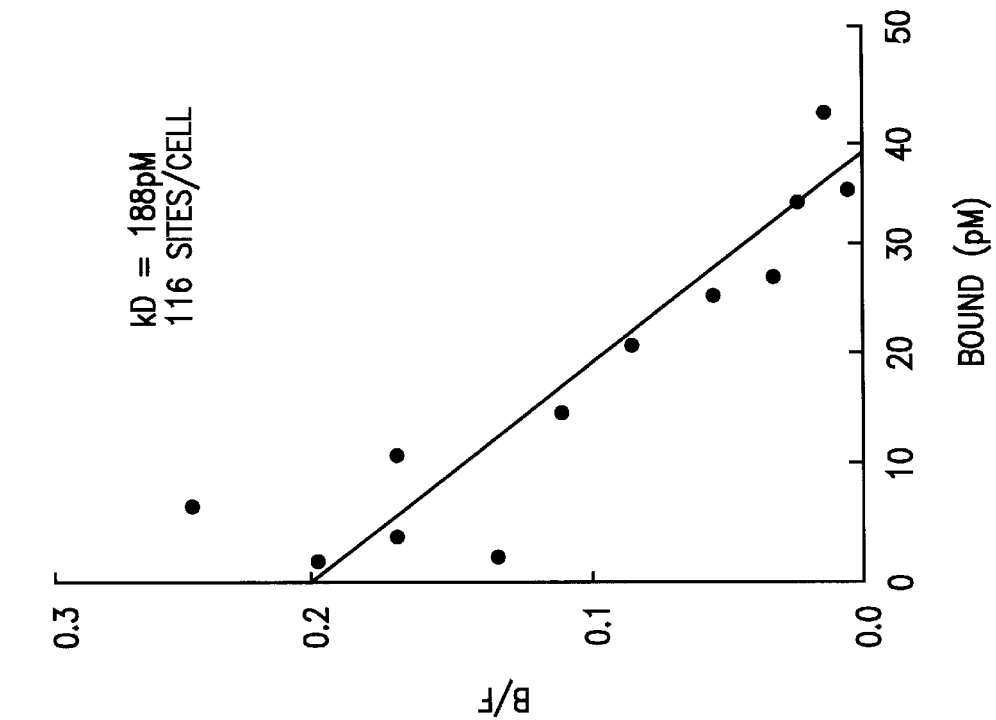
Figure 8A:
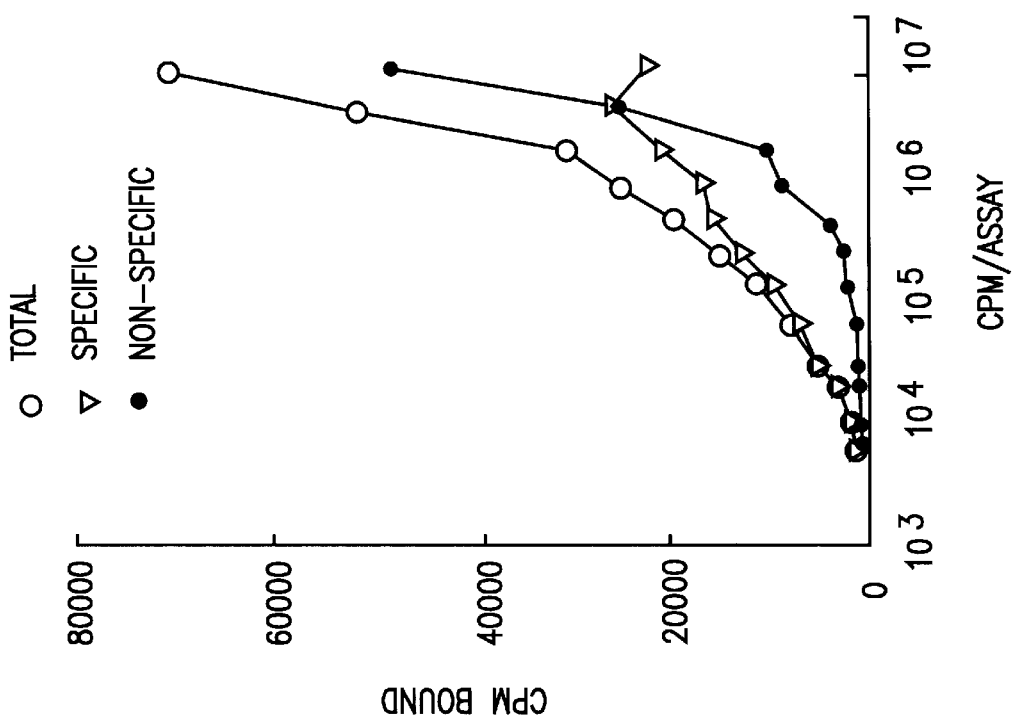

FIGS. 8A and 8B—Equilibrium Binding of $^{125}$I-IL-12 to Detergent Solubilized IL-12R from K6 Cells FIG. 8A shows K6 cells 1.5×10$^8$ cells/ml) were solubilized with 8 mM CHAPS extraction buffer and the cell extract (0.2 ml) was immunoprecipitated for 16 hrs at 4° C. with mAb 2*4E6 immobilized on goat anti-mouse IgG coupled to agarose as described in "Methods". Following this incubation, the beads were pelleted, washed and resuspended in IP buffer containing $^{125}$I-IL-12 at concentrations ranging from 7 pM to 7.5 nM. The IL-12R immobilized on the 2*4E6 coated beads was incubated with $^{125}$I-IL-12 for 2 hrs at RT and IL-12R bound radioactivity was determined in the presence of 50 nM unlabelled IL-12. FIG. 8B shows analysis of the binding data according to the method of Scatchard as determined by Ligand with a single-site model.

Figure 9:
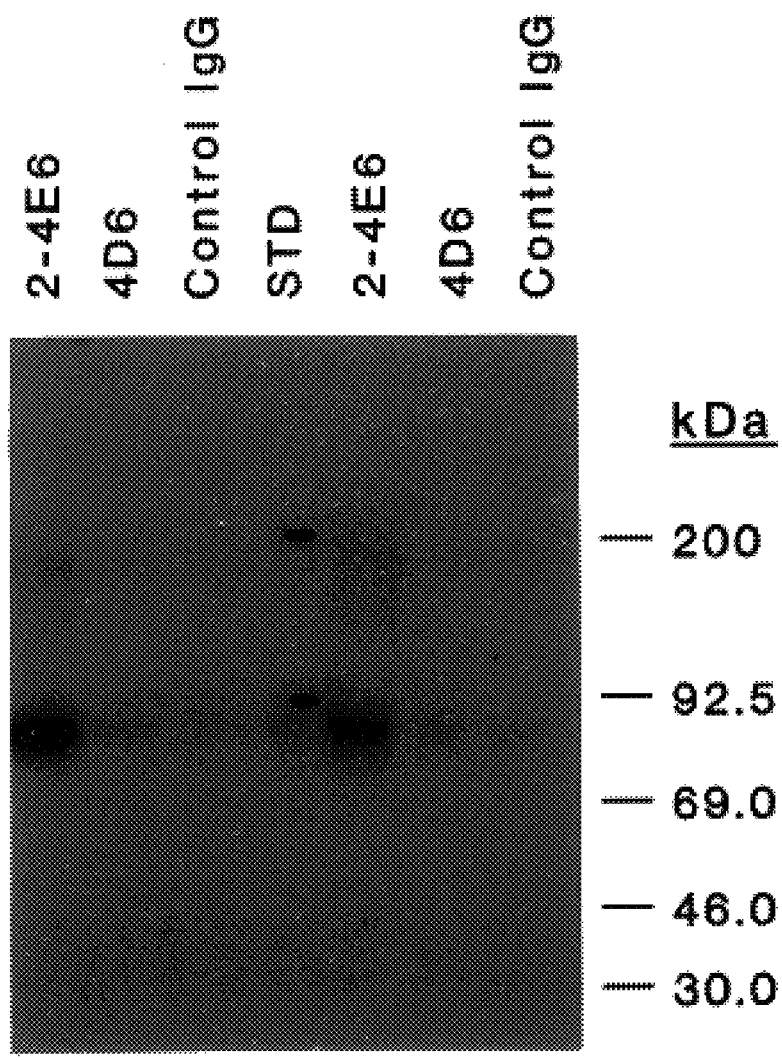

FIG. 9—Western Blot Analysis of Detergent Solubilized IL-12R with mAb 2*4E6

PHA-activated PBMC (1×10$^8$ cells/ml) were solubilized with 8 mM CHAPS extraction buffer and the cell extract (1 ml) was immunoprecipitated as described in FIG. 8. Following this incubation, the beads were pelleted, washed and the bound proteins released by treatment with 0.1 M glycine pH 2.3. The released proteins were separated by non-reducing SDS/PAGE on 8% gels transferred to nitrocellulose membrane and probed with $^{125}$I-2*4E6 as described in "Methods". The molecular sizes indicated in the margins were estimated from molecular weight standards (Amersham Prestained High Molecular Weight Standards) run in parallel lanes. Exposure time was 7 days.

Figure 10B:
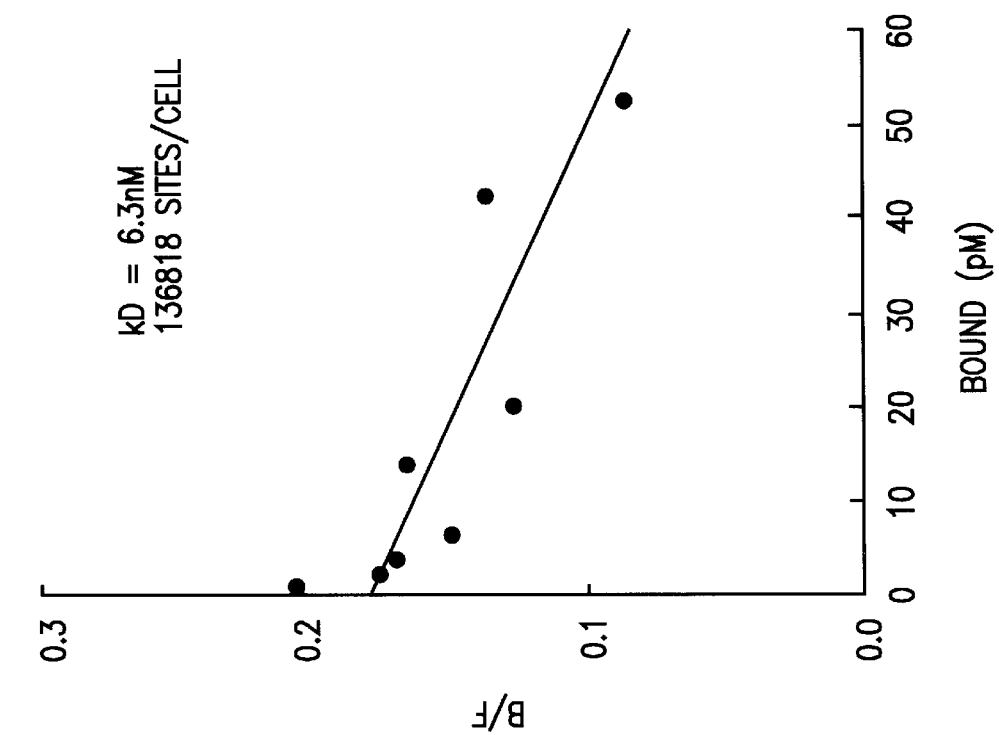
Figure 10A:
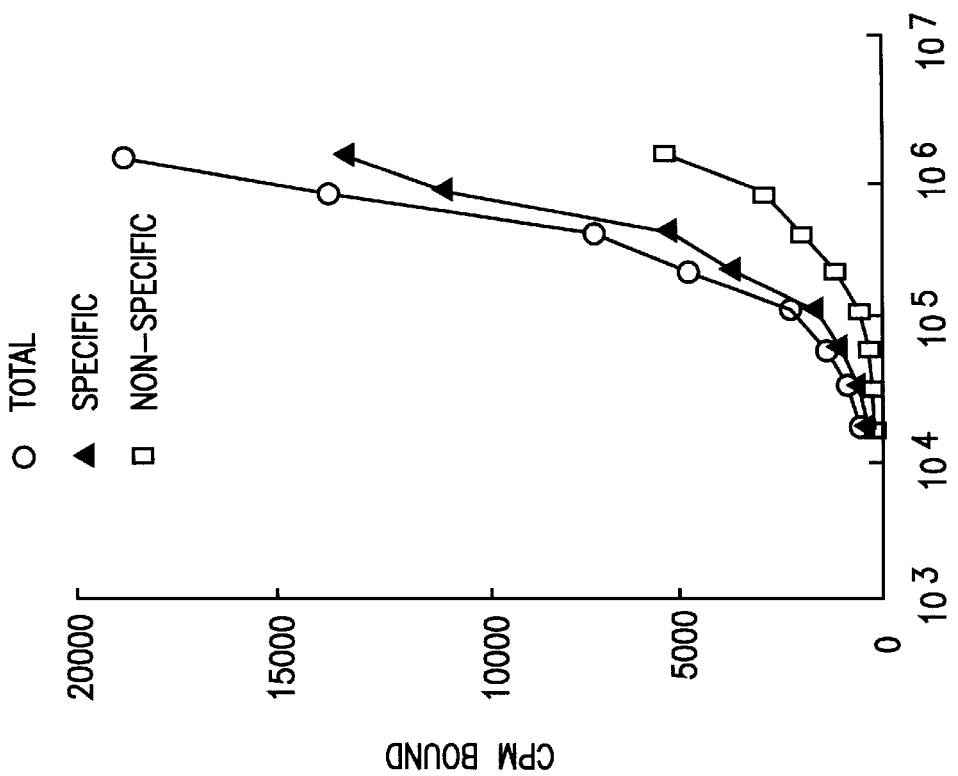

FIGS. 10A and 10B—Equilibrium Binding of $^{125}$I-IL-12 to Human Recombinant IL-12 Receptor Expressed in COS Cells FIG. 10A shows COS cells which were transtected with a plasmid expressing human rIL-12R as described in "Methods". Three days later, transfected cells (1×10$^4$ cells) were incubated for 2 hrs. at room temperature with increasing concentration of $^{125}$I-IL-12 in the absence (○) or presence (□) of 50 nM unlabeled IL-12. Total (○) and non-specific (□) cell bound radioactivity were determined as described in "Methods". Specific binding of $^{125}$I-IL-12 (▲) was calculated by subtracting non-specific binding from total binding. FIG. 10B shows analysis of the binding data according to the method of Scatchlard as determined by Ligand with a single-site model.

Figure 11B:
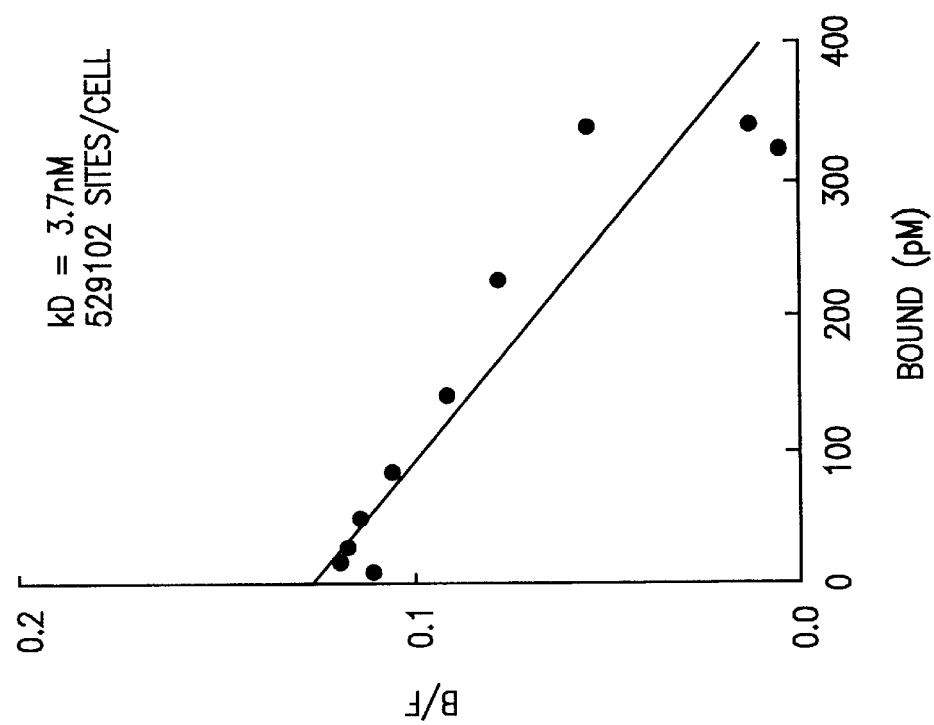
Figure 11A:
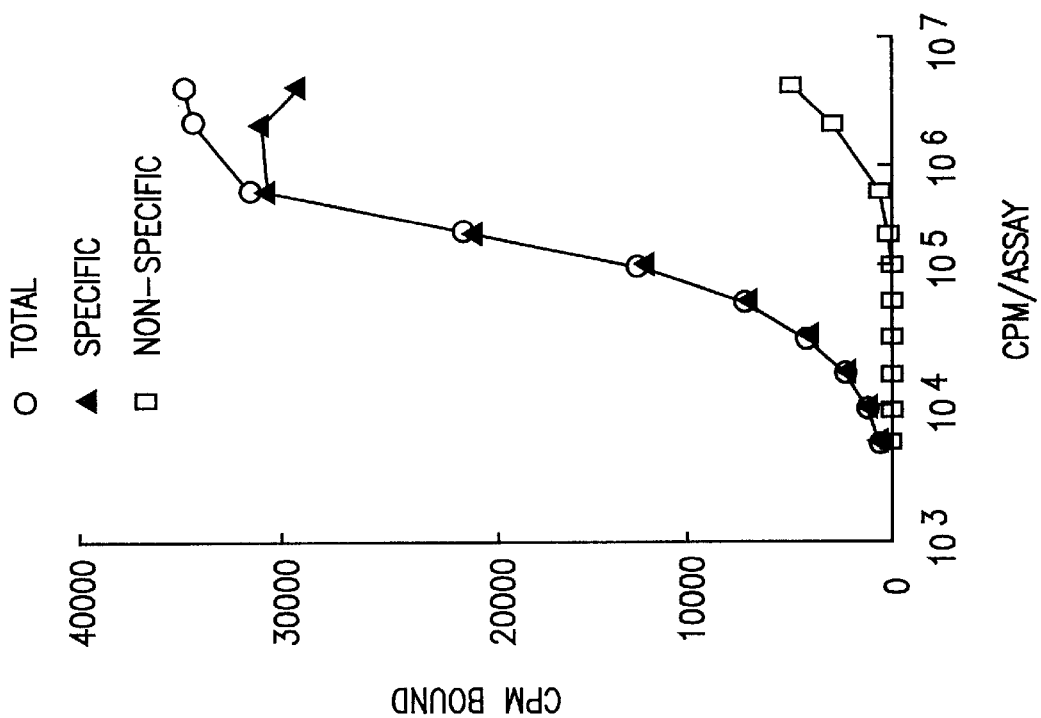

FIGS. 11A and 11B—Equilibrium Binding of $^{125}$I-2*4E6 to Human Recombinant IL-12 Receptor Expressed in COS Cells.

FIG. 11A shows COS cells which were transfected with a plasmid expressing human rIL-12R as described in "Methods". Three days later, transfected cells (1×10$^4$ cells) were incubated for 2 hrs at room temperature with increasing concentrations of $^{125}$I-2*4E6 in the absence (○) or presence (□) of 50 nM unlabeled 2*4E6. Total (○) and non-specific (□) cell bound radioactivity were determined as described in "Methods". Specific binding of $^{125}$I-2*4E6 (▲) was calculated by subtracting non-specific binding from total binding. FIG. 11B shows analysis of the binding data according to the method of Scatchard as determined by Ligand with a single-site model.

Figure 12A:
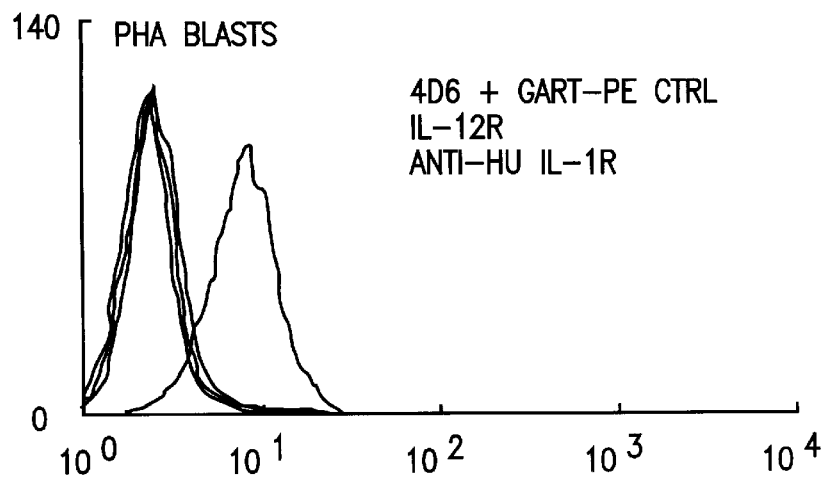
Figure 12B:
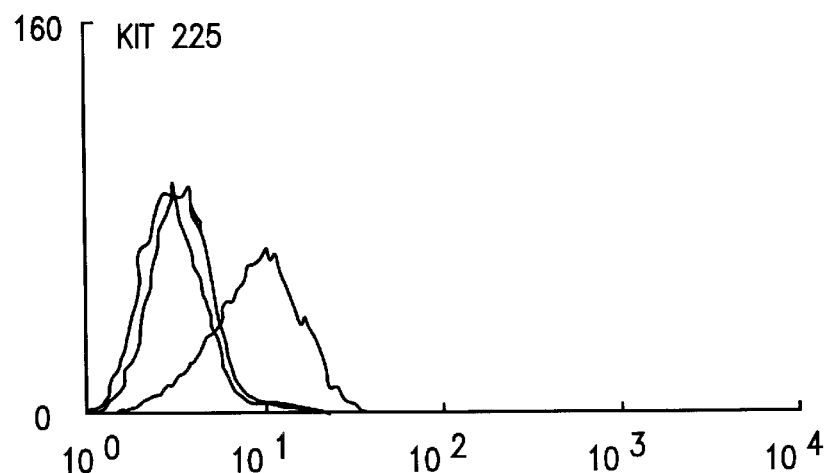
Figure 12C:
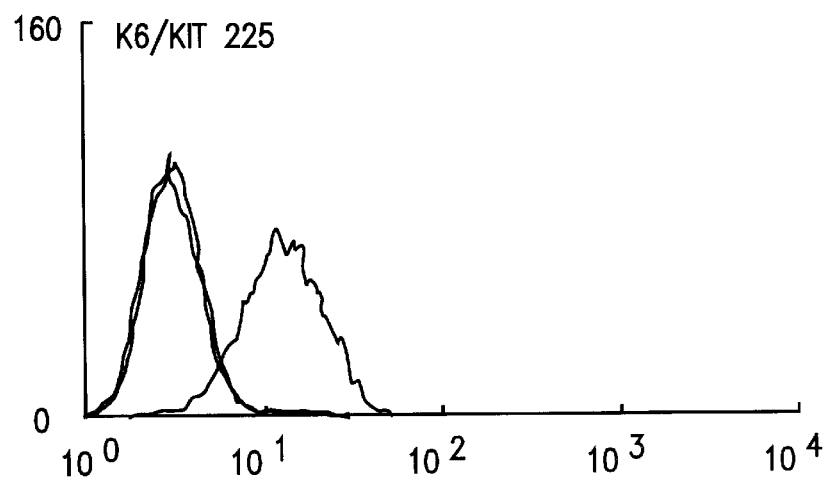

FIGS. 12A, 12B and 12C—Detection of IL-12 Receptor on Human Cells by Flow Cytometry Day 4 PHA-activated lymphoblasts (FIG. 12A), Kit-225 (FIG. 12B) and K6 cells (FIG. 12C) were analyzed for IL-12R expressing cells by the indirect fluorescent antibodylabeling technique described in "Methods". FIGS. 12A, 12B, and 12C, for the respective cells above, depict specific staining for IL-12R obtained in the presence of mAb 2*4E6 (IL-12R) and non-specific staining obtained in the presence of a control antibody specific for IL-1 receptor (anti-Hu IL-1R), a control antibody specific for human IL-12 (4D6+ GART-PE CTRL) and the goat anti-mouse antibody conjugated with PE (GART-PE CTRL).

DETAILED DESCRIPTION OF THE INVENTION

The present invention relates to novel antisera and monoclonal antibodies to the human IL-12 receptor. The antisera of the invention can be conveniently produced by immunizing host animals with PHA-activated human PBMC. Suitable host animals include rodents, such as, for example, mice, rats, rabbits, guinea pigs and the like, or higher mammals such as goats, sheep, horses and the like. Initial doses and booster shots can be given according to accepted protocols for eliciting immune responses in animals, e.g., in a preferred embodiment mice received an initial dose of 6 $\times 10^7$ cells/mouse i.p. and five subsequent booster shots of between 2–5$\times 10^7$ cells over a six month period. Immunized mice were observed to develop an immune response against the human IL-12R as determined by inhibition of $^{125}$I-IL-12 binding to PHA-activated PBMCs (FIG. 1) and immunoprecipitation of the complex of $^{125}$I-IL-12 crosslinked to IL-12R, which methods provide a convenient way to screen for hosts which are producing antisera having the desired activity.

Monoclonal antibodies are produced conveniently by immunizing Balb/c mice according to the above schedule followed by injecting the mice with 1$\times 10^7$ cells i.p. and 2.5$\times 10^6$ cells i.v. on two successive days starting four days prior to the cell fusion. Other protocols well known in the antibody art may of course be utilized as well. The complete immunization protocol detailed herein provided an optimum protocol for serum antibody response for the antibody to the human IL-12 receptor. Other immunization protocols resulted in a lower serum antibody response than the protocol set forth below: For example, 1) immunizations with lower numbers of PHA-activated lymphoblasts (0.7 to 1.8$\times 10^7$ cells/booster immunization); 2) immunizations with fewer numbers of booster immunizations or over a short period of time (40 days) with 2 to 6$\times 10^7$ cells/immunization; and 3) immunizations with cell membranes derived from PHA-activated lymphoblasts (membranes equivalent to 1 to 4$\times 10^8$ cells/immunization) all produced serum antibody responses but not as significant as the protocol below. Similar results were obtained when immunizing rats.

B lymphocytes obtained from the spleen, peripheral blood, lymph nodes or other tissue of the host may be used as the monoclonal antibody producing cell. Most preferred are B lymphocytes obtained from the spleen. Hybridomas capable of generating the desired monoclonal antibodies of the invention are obtained by fusing such B lymphocytes with an immortal cell line, that is a cell line that which imparts long term tissue culture stability on the hybrid cell. In the preferred embodiment of the invention the immortal cell may be a lymphoblastoid cell or a plasmacytoma cell such as a myeloma cell, itself an antibody producing cell but also malignant. Murine hybridomas which produce IL-12R monoclonal antibodies are formed by the fusion of mouse myeloma cells and spleen cells from mice immunized against hIL-12R expressed on the surface of activated peripheral blood mononuclear cells. Chimeric and humanized monoclonal antibodies can be produced by cloning the antibody expressing genes from the hybridoma cells and employing recombinant DNA methods now well known in the art to either join the subsequence of the mouse variable region to human constant regions or to combine human framework regions with complementary determining regions (CDR's) from a donor mouse or rat immunoglobulin. (See, for example, EPO Publication No. 0239400). An improved method for carrying out humanization of murine monoclonal antibodies which provides antibodies of enhanced affinities is set forth in International Patent Application No. WO 92/11018.

Polypeptide fragments comprising only a portion of the primary antibody structure may be produced, which fragments possess one or more immunoglobulin activities. These polypeptide fragments may be produced by proteolytic cleavage of intact antibodies by methods well known in the art, or by inserting stop codons at the desired locations in expression vectors containing the antibody genes using site-directed mutageneses to produce Fab fragments or (Fab')$_2$ fragments. Single chain antibodies may be produced by joining VL and VH regions with a D'NA linker (see Huston et al., *Proc. Natl. Acad. Sci. U.S.A.*, 85, 5879–5883 (1988) and Bird et al., *Science*, 242, 423–426 (1988).

It is also within the skill of the art to utilize the monoclonal antibodies of the present invention as therapeutic agents. They may be formulated for parenteral administration in a manner known in the art such as by dissolving the purified monoclonal antibody product either intact or as a fragment in water for injection and sterile filtering. The dosage form may contain known excipients for parenteral administration of proteins such as buffers, stabilizers and carrier protein. The administered dosage will be selected by the attending physician by giving due consideration to the disease severity and nature as well as the age, size and condition of the patient. As immunoglobulins have demonstrated extended half-lifes in patients dosing every 10–14 days is usually sufficient. It is also within the skill of the art to modify the monoclonal antibody by forming a hybrid with a toxin molecule such as with a pseudomonas exotoxin or with the A chain of ricin to provide a hybrid molecule capable of destroying the cells expressing the IL-12R in a selective manner.

The invention also pertains to a method for detecting peripheral blood cells which express the IL-12 receptor, which comprises contacting a sample which contains the subject cells with substances capable of forming complexes with the IL-12 receptors so as to form cellular complexes between the substances and the IL-12 receptors, and detecting such cellular complexes. Another embodiment of the invention provides a method of evaluating cell activity in a subject which comprises detecting peripheral blood cells according to the method described above.

In the preferred embodiments, the substances are capable of forming complexes only with the IL-12 receptors present on the surface of peripheral blood cells in which the receptors were expressed. Particularly preferred are substances which comprise IL-12 monoclonal antibody.

One embodiment of the invention provides a method of evaluating immune cellular activity which comprises:
 a. isolating peripheral blood mononuclear cells;
 b. treating the cells with the IL-12 monoclonal artibody; and
 c. determining the amount of monoclonal antibody bound to the cells.

The invention also involves a method for diagnosing an immune system abnormality in a subject which comprises determining the number of T cells, NK cells, or B-cells in a sample derived from the subject. This method involves contacting the sample with substances capable of forming complexes with the IL-12 receptors and determining the percentage of T cells, NK cells or B cells in the sample which have the IL-12 receptor. Comparing the percentages so determined with the percentage of cells which have the IL-12 receptor in a sample from a normal subject who does not have the immune system abnormality, the differences in the percentage of cells so determined being indicative of the immune system abnormality. Preferably, the subject is an animal, e.g., a human.

As a molecule associated with T cell, NK cell and B cell function, the measurement of IL-12R expression has diagnostic importance. Because IL-12R is distinctive to activated T cells, NK cells or B cells, it is a unique marker for these cells in a population of lymphocytes.

Moreover, the level of expression of IL-12R provides a measure of T cell, NK cell or B cell activity. This information may be important for evaluating the immune status of an individual. For instance, in the treating of certain disease, such as cancer, agents which affect the immunocompetency are often used. Assays for IL-12R expression may allow physicians to monitor the immune status of the patient and to adjust treatment to minimize the risk of opportunistic infection, often a threat to immunocompromised patients.

Assays for IL-12R expression may be conventional immunochemical assays for cell surface antigens. Peripheral blood mononuclear cells can be isolated from patient and incubated with IL-12R monoclonal antibody under conditions which allow the antibody to bind the surface antigen. Antibody bound to the cell surface provides a measure of IL-12R expression. Binding of the antibody to cells may be evaluated by employing an IL-12R monoclonal antibody labeled with a radioactive, fluorescent or other compound capable of being detected.

The invention also involves a method for detecting soluble IL-12 receptor concentration in samples derived from subjects with immune system disorders, cancer, or other diseases that would be marked by an increase or decrease in soluble form of IL-12R. Assays for soluble IL-12R may be conventional sandwich immunochemical assays or $^{125}$I-IL-12 binding assays to immobilized IL-12R.

Information regarding the IL-12R can be found in U.S. patent application Ser. No. 08/094,713, filed Jul. 19, 1993, which has been now been refiled as a continuation-in-part application Ser. No. 08/248,532, filed May 31, 1994, the contents of both applications being expressly incorporated by reference herein. In accordance with the disclosure of U.S. application Ser. No. 08/094,713, filed Jul. 19, 1993, the cDNA sequence of the human IL-12 receptor (ID-12R) is set forth as SEQ ID No. 1 and the amino acid sequence of this IL-12R is set forth as SEQ ID No. 2.

Certain embodiments of this invention are exemplified in the Examples and Experimental Discussion which follow. In these sections, possible mechanisms and structures are postulated. The Examples and the Experimental Discussion are set forth to aid in an understanding of the invention but are not intended to, and should not be construed to, limit in any way the invention as set forth in the claims which follow.

EXAMPLE 1

Preparation, Characterization & Purification of Hybridoma Antibodies

Balb/c mice (Charles River Laboratories) were immunized by the intraperitoneal route with PHA-activated human PBMC (PHA-activated PBMC) at $6\times10^7$ cells/mouse. Mice received 5 subsequent booster injections of between $2-5\times10^7$ cells over a six month period. For preparation of activated spleen cells, 2 mice were injected intraperitoneally and intravenously with $1\times10^7$ and $2.5\times10^6$ cells, respectively, on two successive days, starting four days prior to the cell fusion. Spleen cells were isolated from these mice and fused with SP2/0 cells at a ratio of 1:1 with 35% v/v polyethylene glycol 4000 (E. Merck) according to the method of Fazekas et al., *J. Immunol.* Methods 35, 1 (1980). The fused cells were plated at a density of $6\times10^5$ cells/ml/well in 48-well cluster dishes in IMDM supplemented with 10% FBS, glutamine (2 mM), β-mercaptoethanol (0.1 mM), gentamicin (50 g/ml), 5% ORIGEN hybridoma cloning factor (IGEN, Inc.), 5% P388D1 supernatant (10) and 100 Units/ml rHuIL-6. Hybridoma supernatants were assayed for specific anti-IL-12 receptor antibodies by: 1) immunoprecipitation of the soluble complex of $^{125}$I-HuIL-12 crosslinked to IL-12 receptor ($^{125}$I-IL-12/IL-12R), 2) inhibition of $^{125}$I-HuIL-12 binding to PHA-activated PBMC's, and 3) differential binding to IL-12 receptor positive cells versus receptor negative cells. Hybridoma cell lines secreting specific anti-receptor antibodies were cloned by limiting dilution. Antibodies were purified from ascites fluids by affinity chromatography on Protein G bound to cross-linked agarose according to the manufacturer's protocol (Genex).

EXAMPLE 2

Preparation of Human PHA Lymphoblasts and IL-12 Receptor Binding Assays

Human peripheral blood mononuclear cells were isolated (see Gately et al, J. Natl. Cancer Inst. 69, 1245 (1982)) and cultured at 37° C. at a density of $5 \times 105$ cells/ml in (tissue culture medium (TCM) containing 0.1% PHA-P (Difco). After 3 days, the cultures are split 1:1 with fresh TCM, and human rIL-2 was added to each culture to give a final concentration of 50 units/ml. The cultures were then incubated for an additional 1–2 days, prior to use in assays.

PHA-activated human PBMC were washed once in binding buffer (RPMI-1640, 5% FBS, 25 mM HEPES pH 7.4) and resuspended in binding buffer to a cell density of $7\times10^6$ cells/ml. Lymphoblasts ($7\times10^5$ cells) were incubated with various concentrations of $^{125}$I-IL-12 (5–10000 pM) at room temperature for the designated times. Cell bound radioactivity was separated from free $^{125}$I-IL-12 by centrifugation of the assay mixture through 0.1 ml of an oil mixture (1:2 mixture of Thomas Silicone Fluid 6428-R15: A. H. Thomas, and Silicone Oil AR 200:Gallard-Schlessinger) at 4° C. for 90 sec at 10,000×g. The tip containing the cell pellet was excised, and cell bound radioactivity was determined in a gamma counter. Non-specific binding was determined by inclusion of 100 nM unlabeled IL-12 in the assay. Incubations were carried out in duplicate or triplicate. Receptor binding data were analyzed by using the non-linear regression programs EBDA and LIGAND as adapted for the IBM personal computer by McPherson, J. Pharmacol Methods 14, 213 (1985) from Elsevier-BIOSOFT.

EXAMPLE 3
Affinity Cross-Linking of $^{125}$I-IL-12 to IL-12 Receptor Bearing Cell Lines IL-12 receptor bearing cells were incubated with $^{125}$I-IL-12 (100–500 pM) in the presence or absence of excess unlabeled IL-12 for 2 hr at room temperature. The cells were then washed with ice-cold PBS pH 8.3 (25 mM Sodium Phosphate pH 8.3, 0.15M NaCl and 1 mM MgCl$_2$) and resuspended at a concentration of $0.5-1.0\times10^7$ cells/ml in PBS pH 8.3. BS3 (Pierce) in dimethyl sulfoxide was added to a final concentration of 0.4 mM. Incubation was continued for 30 min. at 4° C. with constant agitation. The cells were washed with ice-cold 25 mM Tris-HCl (pH 7.5), 0.15 m NaCl and 5 mM EDTA and then solublized at $0.5-1.0\times10^8$ cells/ml in solubilization buffer (50 mM Tris-HCl (pH 8.0) containing 8 mM CHAPS, 0.25 M NaCl, 5 mM EDTA, 40 μg/ml PMSF, 0.05% NaN3, and 1% BSA) for 1 hr at 4° C. The extracts were centrifuged at 12,000×g for 45 min. at 4° C. to remove nuclei and other debris.

EXAMPLE 4
Immunoprecipation Assay of the Soluble Complex of $^{125}$I-IL-12 Crosslinked to Human IL-12R For the immunoprecipitation assay, hybridoma culture supernatant (0.5 ml), diluted antisera, or purified IgG was added to a microfuge tube containing 0.1 ml of a 50% suspension of either goat-anti-mouse IgG coupled to agarose (SIGMA CHEM. CO.) or Protein G coupled to Sepharose 4B (Pharmacia). The assay volume was brought up to 1.0 ml with IP buffer (8 mM CHAPS in PBS (0.25 MNaCl), 1% BSA, & 5 mM EDTA) and the mixture was incubated on a rotating mixer for 2 hr at room temperature. The beads were pelleted by centrifugation, resuspended in 1 ml IP buffer containing $^{125}$I-IL-12/IL-12R (10–20,000 cpm) and the mixture was incubated on a rotating mixer for 16 hr at 4° C. After this incubation, the beads were pelleted by centrifugation and washed twice in IP buffer without BSA. The $^{125}$I-labelled receptor complex bound to the solid phase antibodies was released by adding 100 μl of 2×Laemmli sample buffer (Nature 227, 680 (1970)) with and without 10% -mercaptoethanol and heating for 5 min. at 95° C. The immunoprecipitated proteins were analyzed by SDS-PAGE on 8% or 4–15% gradient polyacrylamide gels and visualized by autoradiography.

EXAMPLE 5
Assays for IL-12R Solubilized from Cells Expressing IL-12 Receptor To confirm that the antibodies identified by the immunoprecipitation assay were specific for IL-12R, an immunoprecipitation/soluble IL-12R binding assay was developed. As described in Example I above, antibodies (as hybridoma supernatant, purified IgG (50 μg) or antisera) were immobilized by binding to goat anti-mouse IgG coupled to agarose (100 μl; Sigma Chemical Co.) or protein G coupled to Sepharose 4B (100 μl; Pharmacia). For some experiments, antibodies were covalently crosslinked to protein G-Sepharose 4B, before being used in the assay (See Stern and Podlaski, Techniques in Protein Chemistry (1993). The immobilized antibodies were resuspended in IP buffer (0.3 ml) and 0.2 ml of a detergent solubilized extract of PHA-activated PBMCs or K6 cells that contained IL-12R was added. To prepare the detergent solubilized IL-12R preparation, the cells were washed with ice-cold 25 mM Tris-HCl (pH 7.5), 0.15 M NaCl and 5 mM EDTA and then solublized at $1.5\times10^8$ cells/ml in solubilization buffer (50 mM Tris-HCl, pH 8.0, containing 8 mM CHAPS, 0.25 M NaCl, 5 mM EDTA, 40 μg/ml PMSF, 0.05% NaN3, and 1% BSA) for 1 hr at 4° C. The extracts were centrifuged at 120,000×g for 60 min. at 4° C. to remove nuclei and other debris. The mixture was incubated on a rotating mixer for 16 hr at 4° C. After this incubation, the beads were pelleted by centrifugation and resuspended in IP buffer (0.15 ml) containing $^{125}$I-HuIL-12 at concentrations ranging from 0.05 to 7.5 nM. The IL-12R immobilized on the antibody coated beads was incubated with $^{125}$I-HuIL-12 for 2 hrs. at room temperature on a shaker. Following this incubation, the beads were pelleted, washed twice with IP buffer and the bound radioactivity determined in a gamma counter. Non-specific binding was determined by inclusion of 70 nM unlabeled human IL-12 in the assay. Solubilized IL-12R binding data were analyzed according to the method of Scatchard, (Assn. N.Y. Acad. Sci. 51, 660 (1949)) by using the nonlinear regression programs EBDA and Ligand as adapted for the IBM PC by McPherson, supra from Elsevier-BIOSOFT.

EXAMPLE 6
Competitive Inhibition of $^{125}$I-IL-12 Receptor Binding by Antibodies The ability of hybridoma supernatant solutions, purified IgG, or antisera to inhibit the binding of $^{125}$I-IL-12 to PHA-activated lymphoblasts was measured as follows: serial dilutions of culture supernatants, purified IgG or antisera were mixed with activated lymphoblasts ($1-1.5\times10^6$ cells) in binding buffer (RPMI-1640, 5% FBS+25 mM Hepes pH 7.4) and incubated on an orbital shaker for 1 hour at room temperature. $^{125}$I-HuIL-12 ($1\times10^5$ cpm) was added to each tube and incubated for 1–2 hours at room temperature. Non-specific binding was determined by inclusion of 10 nM unlabeled IL-12 in the assay. Incubations were carried out in duplicate or triplicate. Cell bound radioactivity was separated from free $^{125}$I-IL-12 by centrifugation of the assay through 0.1 ml of an oil mixture as described above. The tip containing the cell pellet was excised, and cell bound radioactivity was determined in a gamma counter.

EXAMPLE 7
Labeling of Human IL-12 and Mab 2*4E6 with $^{125}$I

Human IL-12 and purified 2*4E6 IgG were labelled with $^{125}$I by a modification of the Iodogen method (Pierce Chemical Co., Rockford, Ill.). Iodogen was dissolved in chloroform and 0.05 mg dried in a 12×15 mm borosilicate glass tube. For radiolabeling, 1.0 mCi Na[$^{125}$I] (Amersham, Chicago, Ill.) was added to an Iodogen-coated tube containing 0.05 ml of Tris-iodination buffer (25 mM Tris-HCL pH 7.5, 0,4 M NaCl and 1 mM EDTA) and incubated for 4 min at room temperature. The activated $^{125}$I solution was transferred to a tube containing 0.05 to 0.1 ml IL-12 (7 µg) or IgG (100 µg) in Tris-iodination buffer and the reaction was incubated for 9 min at room temperature. At the end of the incubation, 0.05 ml of Iodogen stop buffer (10 mg/ml tyrosine 10% glycerol in Dulbecco's PBS, pH 7.40) was added and reacted for 3 min. The mixture was then diluted with 1.0 ml Tris-iodination buffer, and applied to a Bio-Gel P10DG desalting column (BioRad Laboratories) for chromatography. The column was eluted with Tris-iodination buffer, and fractions (1 ml) containing the peak amounts of labelled protein were combined and diluted to 1×108 cpm/ml with 1% BSA in Tris-iodination buffer. The TCA preciptable radioactivity (10% TCA final concentration) was typically in excess of 95% of the total radioactivity. The radiospecific activity was typically~1500 to 2500 cmp/fmol for 2*4E6 IgG and 5000 to 7000 cpm/fmole for IL-12.

EXAMPLE 8

Binding Assays of $^{125}$I-2*4E6 to Intact Cells

PHA-activated human PBMC were washed once in binding buffer (RPMI 1640, 5% FBS and 25 mM Hepes, pH 7.4) and resuspended in binding buffer to a cell density of 1.5×10$^7$ cells/ml. Lymphoblasts (1.5×106 cells) were incubated with various concentrations of $^{125}$I-2*4E6-IgG (0.005 to 2 nM) at room temperature for 1.5 hrs. Cell bound radioactivity was separated from free $^{125}$I-2*4E6 IgG by centrifugation of the assay mixture through 0.1 ml silicone oil at 4° C. for 90 seconds at 10,000×g. The tip containing the cell pellet was exercised, and cell bound radioactivity was determined in a gamma counter. Non-specific binding was determined by inclusion of 67 nM unlabeled 2*4E6 IgG in the assay. Incubations were carried out in duplicate or triplicate. Receptor binding data were analyzed by using the nonlinear regression programs EBDA, Ligand and Kinetics as adapted for the IBM personal computer by McPherson, supra from Elsevier BIOSOFT.

EXAMPLE 9

Expression of Recombinant IL-12R in COS Cells and Determination of $^{125}$I-2*4E6 Binding COS cells (4–5×10$^7$) were transfected by electroporation with 25 µg of plasmid DNA expressing recombinant human IL-12R (U. Gubler and A. Chua, unpublished observations) in a BioRad Gene Pulser (250 µF, 250 volts) according to the manufacturer's protocol. The cells were plated in a 600 cm2 culture plate, harvested after 72 hours by scraping, washed and resuspended in binding buffer. Transfected cells (8×10$^4$ were incubated with increasing concentrations of $^{125}$I-labeled 2*4E6 or IL-12 at room temperature for 2 hrs. Cell bound radioactivity was separated from free $^{125}$I-labeled 2*4E6 or IL-12 as described above.

EXAMPLE 10

Western Blot Analysis of Soluble IL-12R with mAb 2*4E6

PHA-activated PBMC were washed 3 times with ice-cold PBS and solubilized at 0.5–1×10$^8$ cells/ml in solubilization buffer (50 mM Tris-HCl pH 8.0 containing 8 mM CHAPS, 0.25 M NaCl, 5 mM EDTA, 40 µg/ml PMSF, 0.05% NaN3 and 1 mg/ml BSA) for 1 hr at 4° C. The extracts were centrifuged at 12,000×g for 45 min. at 4° C. to remove nuclei and other debris. The extracts were incubated with 2*4E6 IgG or control IgG bound to goat-anti-mouse IgG immobilized on cross-linked agarose (Sigma Chemical Co.). The precipitated proteins were released by treatment with 0.1 M glycine pH 2.3, neutralized with 3M Tris, mixed with 1/5 volume of 5×Laemmli sample buffer, and separated by SDS,/PAGE on 8% pre-cast acyrlamide gels (NOVEX). The separated proteins were transferred to nitrocellulose membrane (0.2 µM) for 16 hours at 100 volts in 10 mM TRIS-HCL (pH 8.3), 76.8 mM glycine, 20% methanol and 0.01% SDS. The nitrocellulose membrane was blocked with BLOTTO (50% w/v nonfat dry milk in PBS+0.05% Tween 20) and duplicate blots were probed with $^{125}$I-2*4E6 IgG (1×106 cpm/ml in 8 mM CHAPS in PBS, 0.25 M NaCl, 10% BSA and 5 mM EDTA)+unlabelled 2*4E6 IgG (67nM).

EXAMPLE 11

Analysis of IL-12 Receptor Expression on Human Cells by Fluorescence Activated Cell Sorting with mAb 2*4E6

To stain cells expressing IL-12 receptor, 1×10$^6$ in 100 µl staining buffer (PBS containing 2% FBS and 0.1% NaN3) were incubated with 10 µl of 2*4E6 ascites fluid for 25 min. at 4° C. Cells were then washed twice with staining buffer followed by incubation with a 1:100 dilution of goat F(ab)2 anti mouse Ig-PE (Tago, Burlingame Calif.) for 25 min. at 4° C. The stained cells were washed twice with staining buffer and then analyzed on a FACScan flow cytometer (Beckton Dickinson).

EXAMPLE 12

Figure 1:
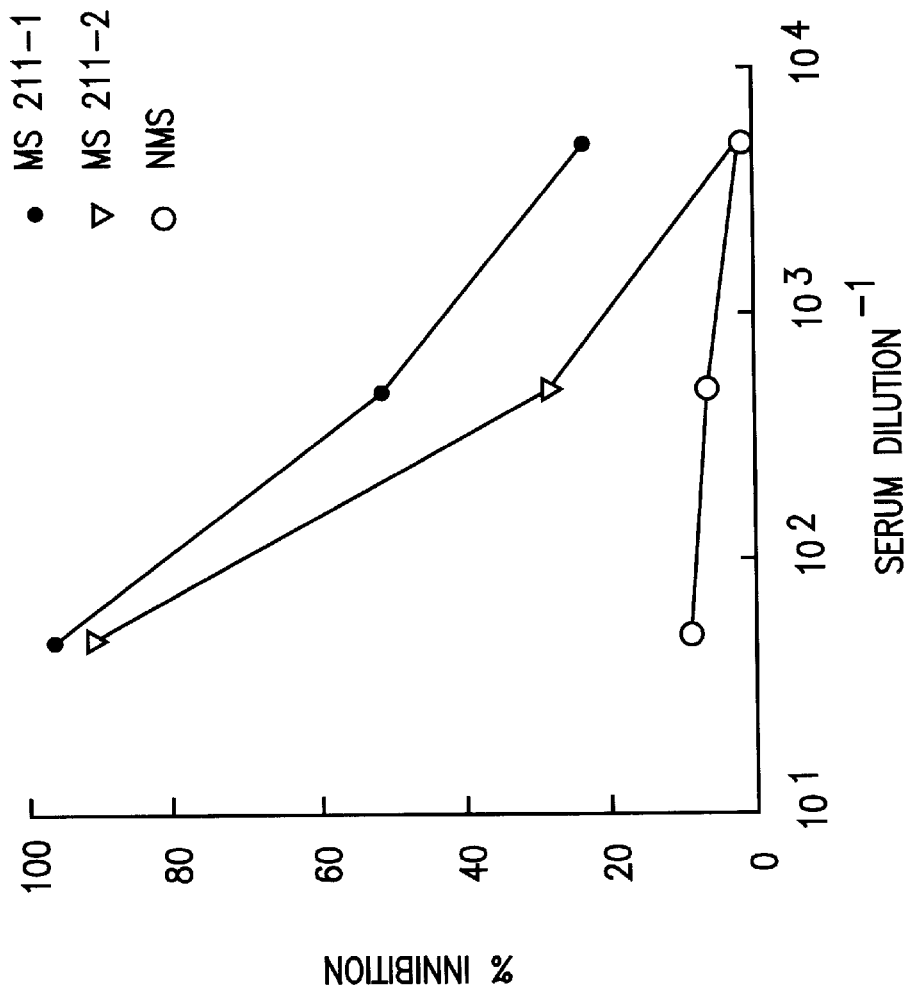
FIG. 1—Inhibition of $^{125}$I-IL-12 Binding to IL-12 Receptor by Mouse Anti-IL-12R Antiserum Ten fold serial dilutions of mouse anti-IL-12R immune serum (#211-1 and #211-2) and normal mouse serum (NMS) were preincubated with PHA-activated PBMC for 60 min at RT before addition of $^{125}$I-IL-12 (100 pM). After addition of $^{125}$I-IL-12, the reaction was incubated for 1–2 hrs at RT and the cell bound radioactivity was determined as outlined in "Methods". The data are expressed as the % Inhibition of $^{125}$I-IL-12 binding in the presence of the immune serum when compared to the specific binding in the absence of serum.

Inhibition of IL-12 Binding to Human PHA-Lymphoblasts by Mouse Anti-IL-12R Antiserum Mice immunized with PHA-activated PBMCs developed an immune response against the human IL-12R as determined by inhibition of $^{125}$I-IL-12 binding to PHA-activated PBMCs (FIG. 1) and immunoprecipitation of the complex of $^{125}$I-IL-12 crosslinked to IL-12R (data not shown). The dilutions for half-maximal inhibition of $^{125}$I-IL-12 binding to PHA-activated PBMCs were 1/500 and 1/250 for animals 211-1 and 211-2, respectively (FIG. 1). These antisera also neutralized IL-12 biologic activity as measured in a PHA-lymphoblast proliferation assay (data not shown). Spleen cells isolated from these mice were fused with SP2/0 myeloma cells and the resulting hybridomas were initially screened for IL-12R specific antibodies by immunoprecipitation of the $^{125}$I-IL-12/IL-12R complex and by inhibition of $^{125}$I-IL-12 binding to IL-12R.

EXAMPLE 13

Identification and Characterization of Monoclonal Anti-Il-12R Antibodies

The immunoprecipitation assay identified 13 hybridomas secreting putative non-neutralizing anti-IL-12R antibodies, whereas the IL-12R binding assay identified 3 putative neutralizing IL-12R antibodies (Table 1). The immunoprecipitation assay measured the ability of the putative anti-IL-12R antibodies that are immobilized on a solid phase to capture the solubilized complex of $^{125}$I-IL-12/IL-12R. To verify that the radioactivity immunoprecipitated by the immobilized antibody was present in the complex of $^{125}$I-

Figure 2:
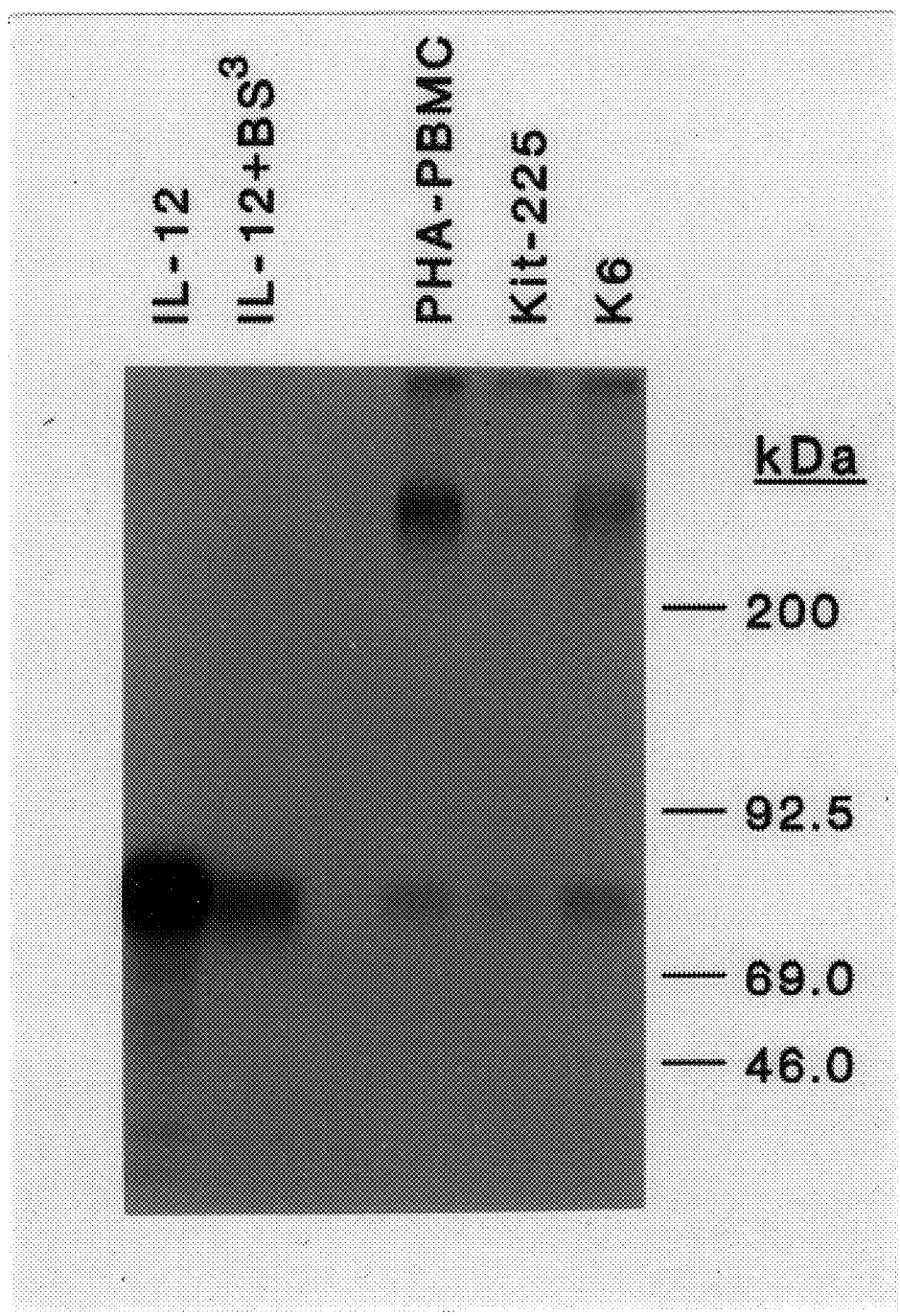
FIG. 2—Characterization of the IL-12 Binding Proteins on IL-12R Positive Human cells by Affinity-Crosslinking PHA-activated PBMC (PHA-PBMC), Kit-225 (Kit-225) and K6 (K6) cells ($1 \times 10^7$ cells/ml) were incubated with $^{125}$I-IL-12 (100–500 pM) for 2 hrs at room temperature in the absence or presence of 25 nM unlabeled IL-12. Cells were then washed, affinity crosslinked with BS3 (0.4 mM final concentration) and a cell extract prepared as described in "Methods". The cell extract was precipitated with wheat germ lectin bound to solid supports as described in "Methods". The precipitated proteins were released by treatment with sample buffer and analyzed by SDS-PAGE and autoradiography on a 8.0% slab gel. The complex of $^{125}$I-IL- 12 crosslinked to the IL-12 receptor migrates as a single major band of approximately 210–250 kDa. The band migrating at 75 KDa is $^{125}$I-IL-12 that was bound but not crosslinked to the IL-12 receptor. $^{125}$I-IL-12 (IL-12) and $^{125}$I-IL-12 that was treated with the BS3 crosslinker (IL-12/BS3) were electrophoresed in parallel lanes as markers for the migration of the 75 kDa IL-12 heterodimer and for any oligomers of IL-12 that may form with the BS3 crosslinker. The molecular sizes indicated in the margins were estimated from standards run in parallel lanes. Exposure time was 7 days.

IL-12/IL-12R, the immunoprecipitated proteins were solubilized, separated by SDS-PAGE and visualized by autoradiography. The preparations of the $^{125}$I-IL-12/IL-12R complexes solubilized from PHA-activated PBMC, Kit-225 and K6 cells were resolved into two major radioactive bands, 210–250 kDa and 7.5 kDa (FIG. 2). The 210–250 kDa and 75 kDa complexes were identified as the $^{125}$I-IL-12/ IL-12R complex and $^{125}$I-IL-12 not complexed with the receptor, respectively (FIG. 2). See also Chizzonite et al., *J. Immunol.* 148, 3117 (1992). The radioactive 75 kDa band visualized from the cell extracts co-migrated with $^{125}$I-IL-12, indicating that it represented $^{125}$I-IL-12 that bound but was not covalently crosslinked to IL-I2R. The 210–250 kDa band was not a covalent crosslinked oligomer of $^{125}$I-IL-12 because it is not produced when the crosslinking agent BS3 was added directly to $^{125}$I-IL-12 (FIG. 2).

Hybridoma cells secreting putative anti-IL-12R antibodies were then cloned by limiting dilution and screened by both the immunoprecipitation and inhibition of binding assays that identify non-nuetralizing and neutralizing antibodies, respectively. During this cloning and screening process, hybridoma lines secreting putative neutralizing anti-IL-12R antibodies were not recovered, whereas non-neutralizing antibodies were recovered from both the original immunoprecipitation and inhibitory positive hybridomas. After this initial identification and cloning, a direct binding assay was used to determine if the non-neutralizing antibodies only bound to cells expressing IL-12R. This assay demonstrated that the non-neutralizing antibodies could be divided into 2 classes, those that bound only IL-12R postive human cells and those that bound to most human cells (data not shown). Representitive antibodies from each class, 2*4E6 and 2C6, respectively, were produced in ascites fluid, purified by protein G affinity chromatography and extensively characterized.

TABLE 1

INITIAL IDENTIFICATION OF HYBRIDOMAS SECRETING ANTI-IL-12 RECEPTOR ANTIBODIES: SPLENOCYTES FROM MICE #211-1 AND #211-2

| | HYBRIDOMA/ANTIBODY | I.P. ASSAY[1] (cpm bound) | INHIBITION ASSAY[2] |
|---|---|---|---|
| | IL-12R 2C6[3] | 1900 | – |
| 211-1 | 1A5 | 722 | – |
| | 4E6 | 840 | – |
| | 5C1 | 312 | + |
| 211-2 | 3B1 | 1323 | – |
| | 4A3 | 2172 | – |
| | 4D6 | 804 | – |
| | 5D5 | 877 | – |
| | 4A5 | 509 | + |
| | 4C6 | 456 | + |
| | 1D1 | 1395 | – |
| | 5E6 | 2043 | – |
| | 2–4E6 | 2836 | – |
| Control mAb | | 402 | – |

[1]I.P. assay measures the amount of $^{125}$I-IL-12/IL-12R complex bound by the immobilized antibody.
[2]Inhibition assay measures whether the antibody can inhibit $^{125}$I-IL-12 binding to PHA-activated PBMC.
[3]IL-12R 2C6 is an antibody that both immunoprecipitates the $^{125}$IL-12/IL-12R complex and binds to many IL-12R positive and negative human cells. This antibody probably recognizes a component closely associated with the IL-12R.

EXAMPLE 14

Figure 3:
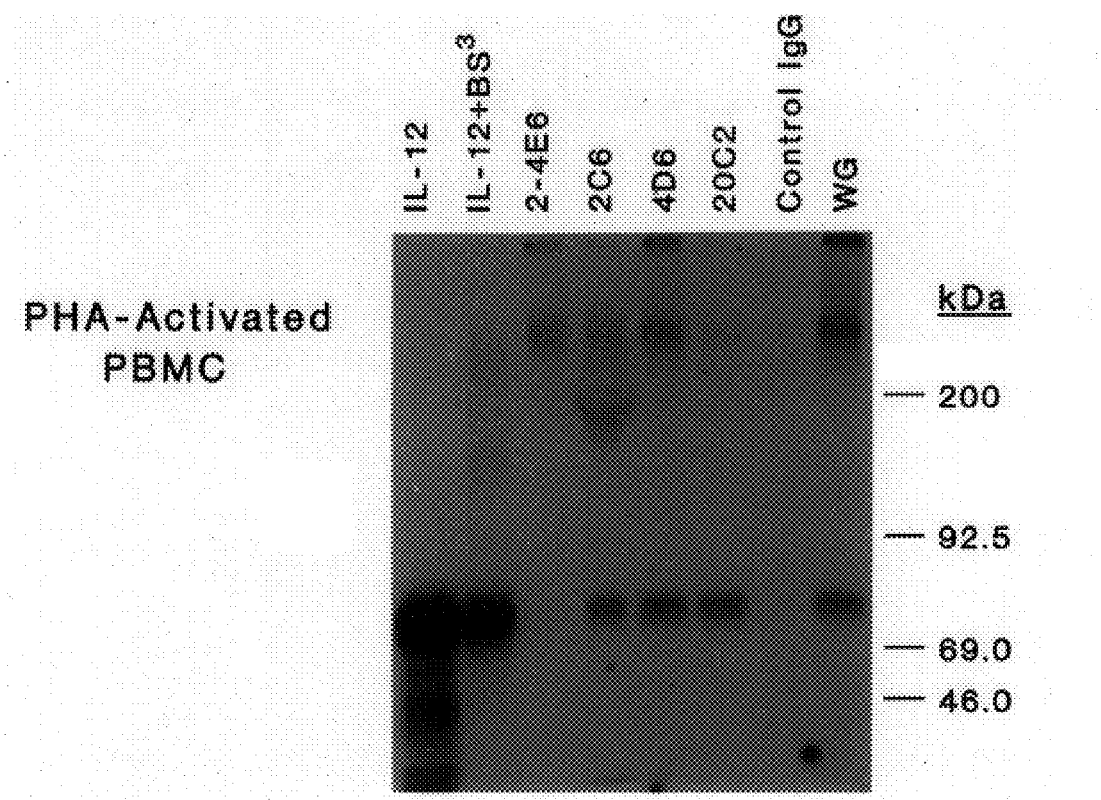
FIG. 3—Immunoprecipitation of the Solubilized $^{125}$I-IL-12/IL-12R Crosslinked Complex by Anti-IL-12R Antibodies Soluble complexes of $^{125}$I-IL-12/IL-12R were prepared from PHA-activiated human PBMC as detailed in "Methods" and FIG. 2, and immunoprecipitated by immobilized antibodies, 2*4E6, 2C6, 4D6, 20C2 and control. The soluble complexes were also precipitated with wheat germ lectin immobilized on crosslinked agarose (WG). The precipitated proteins were analyzed as described in "Methods" and in FIG. 2. Antibodies 4D6 and 20C2 are non-neutralizing and neutralizing anti-IL-12 antibodies, respectively. 4D6 immunoprecipitates $^{125}$I-IL-12/IL-12R complex and free $^{125}$I-IL-12, whereas 20C2 only immunoprecipiiates free $^{125}$I-IL-12. Both 2*4E6 and 2C6 recognize the $^{125}$I-IL-12/IL-12it complex. $^{125}$I-IL-12 (IL-12) and $^{125}$I-IL-12 that was treated with the BS3 crosslinker (IL-12/BS3) were electrophoresed in parallel lanes as markers for the migration of the 75 kDa IL-12 heterodimer and for any oligomers of IL-12 that may form wit the BS3 crosslinker. The molecular sizes indicated in the margins were estimated from standards run in parallel lanes. Exposure time was 7 days.
Figure 4B:
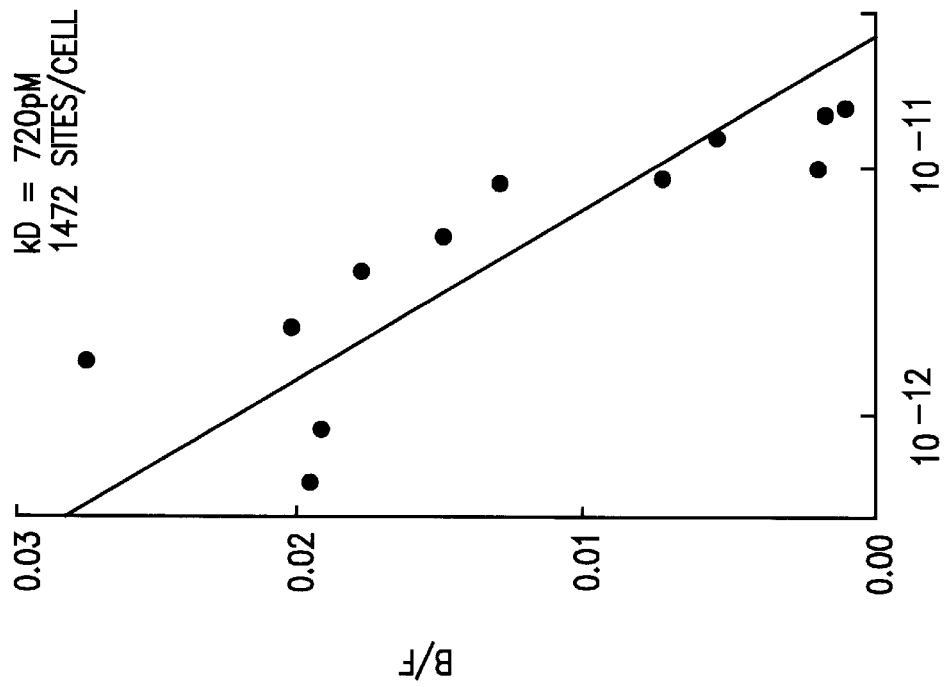
FIGS. 4A and 4B—Equilibrium binding of $^{125}$I-2*4E6 to PHA-activated PBMC at Room Temperature
Figure 4A:
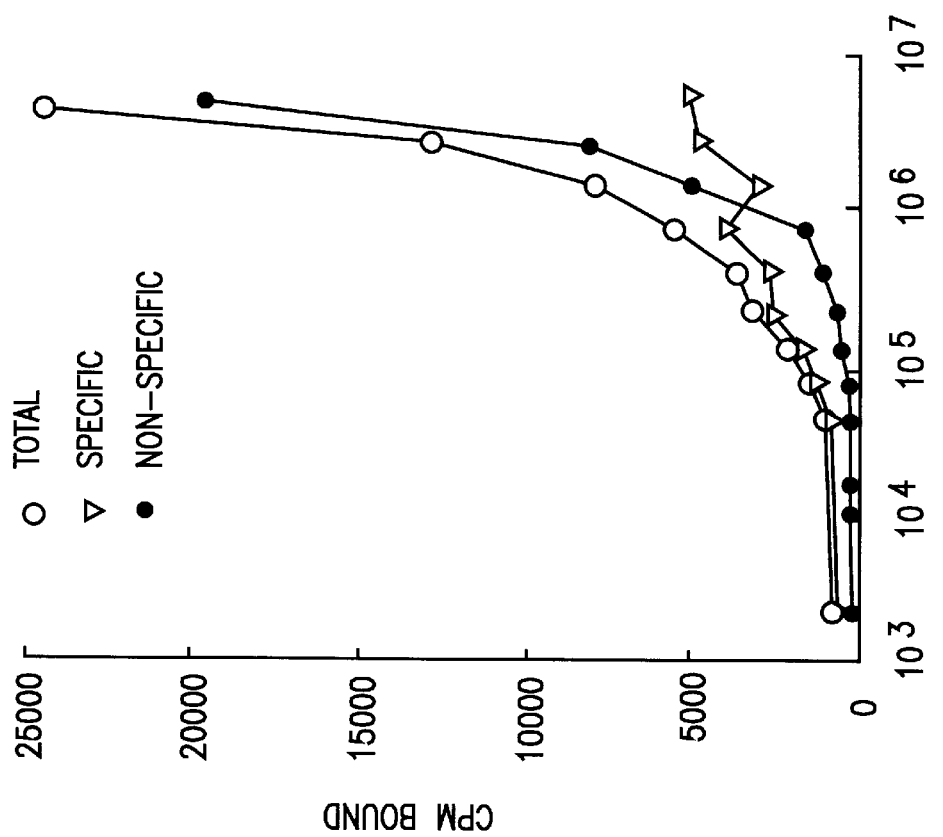
Figure 6:
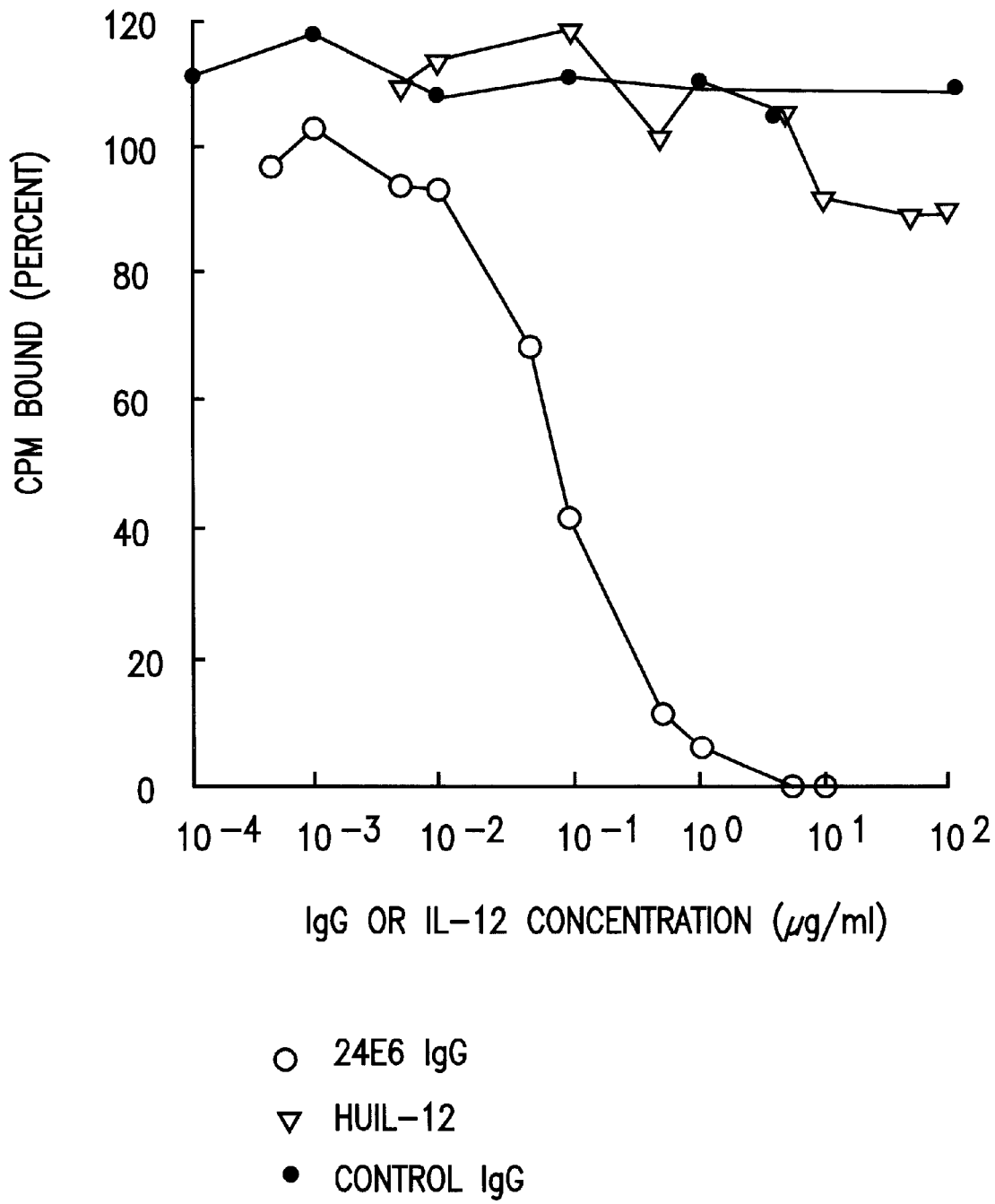
FIG. 6—Inhibition of $^{125}$I-2*4E Binding to K6 Cells by Purified 2*4E6 (24E6), Human IL-12 (HUIL-12) and Control Antibody (Control IgG)

Characteristics of Monclonal Anti-IL-12R Antibody 2*4E6 Binding to Natural IL-12R MAb 2*4E6 immunoprecipitates the $^{125}$I-IL-12/IL-12R complex solubilizied from PHA-activated human lymphoblasts, Kit-225 and K6 cells (FIG. 3, data shown for PHA-activated PBMC), but does not block $^{125}$I-IL-12 binding to IL-12R expressed on these cells. These data suggested that the 2*4E6 antibody was a non-inhibitory or non-neutralizing anti-IL-12R antibody. To confirm that 2*4E6 was an non-inhibitory antibody specific for the IL-12R, 2*4E6 was labelled with $^{125}$I and direct binding assays were performed with IL-12R positive and regative cells. $^{125}$I-2*4E6 binds to IL-12R bearing cells with an affinity that ranges from 337 pM to 904 pM and identifies between 1500 and 5000 binding sites per cell (PHA-activated PBMC, FIGS. 4A and 4B; K6 cells, FIG. 5). IL-12 does not block $^{125}$I-2*4E6 from binding to PHA-activated PBMCs and confirms that 2*4E6 is a non-inhibitory/non-neutralizing antibody (FIG. 6). $^{125}$I-2*4E6 binds to other cells expressing IL-12R, such as Kit 225, and YT cells, but does not bind to IL-12R negative cells (non-activated human PBMC, MRC-5 fibroblasts and HL-60 cells (Table 2).

Equilibrium binding assays have demonstrated that $^{125}$I-IL-12 identifies 3 separate binding sites on the surface of PHA-activated PBMCs, Kit-225 and K6 cells (FIGS. 7A and 7B, data for K6 cells and Table 2). Analysis of this binding data by the method of Scatchard, supra shows these affinities are approximately 5–20 pM, 50–200 pM and 2–6 nM, respectively. The total number of $^{125}$I-IL-12 binding sites per cell are approximately 1500 to 5000, which is in good agreement with the total number of binding sites identified by $^{125}$I-2*4E6 (Table 2). The data also suggests that 2*4E6 recognizes the low affinity (2–5 nM) binding conponent of the IL-12 receptor in much the same manner that the anti-TAC antibody recognizes the low affinity component (p55 subunit) of the IL-2 receptor.

Since the data indicated that mAb 2*4E6 was a non-neutralizing antibody specific for the IL-12R, the molecular weight and $^{125}$I-IL-12 binding characteristics of the protein (s) immunoprecipitated by mAb 2*4E6 from the surface of IL-12R postive cells was investigated. The steady state binding of $^{125}$I-IL-12 to proteins immunoprecipitated by immobilized 2*4E6 from solubilized extracts of PHA-activated PBMCs, Kit-225 and K6 cells was saturable and specific (FIGS. 8A and 8B, data for extracts from K6 cells). Transformation of the binding data by the method of Scatchard, revealed a single site with an apparent affinity of 188 pM. The proteins immunoprecipitated by 2*4E6 from the cell extracts were resolved by SDS-PAGE, transferred to nitrocellulose membrane and probed with $^{125}$I-2*4E6 in a western blot. On the western blot, $^{125}$I-2*4E6 binds to an approximately 90 kDa protein, that is only immunoprecipitated by 2*4E6 and not by an anti-IL-12 antibody or a control antibody (FIG. 9, data shown for PHA-activated PBMCs). In summary, all the data demonstrated that mAb 2*4E6 bound a protein on the surface of IL-12R positive cells that was approximately 90 kDa and bound $^{125}$I-IL-12 in a specific manner.

TABLE 2

COMPARISON OF THE BINDING OF IL-12 AND 2-4C6 TO HUMAN CELLS EXPRESSING IL-12 RECEPTOR

| | IL-12 BINDING[1] | | 2-4E6 BINDING[2] | |
|---|---|---|---|---|
| CELL TYPE | $K_D$ (nM) | Sites/cell | $K_D$ (nM) | Sites/cell |
| Human Cells | | | | |
| non-activated human PBMC[3] | none detected | | none detected | |
| PHA-PBMC (5–7 days) (3 sites) | 0.018 0.084 1.800 | 312 501 1406 | 0.745 | 1472–2246 |
| K6 cells (3 sites) | 0.016 0.057 2.400 | 707 939 4036 | 0.489 | 3116–5259 |
| Kit-225 (3 sites) | 0.023 0.210 2.360 | 100 250 755 | 0.594 | 1950 |
| YT cells (2 sites) | 0.006 0.109 | 24 117 | 0.904 | 4522 |
| RAJI cells | none detectable | | 0.450 | 561 |
| MRC-5 | none detectabl | | none detectable | |
| HL-60 | none detectable | | none detectable | |

[1]Steady state $^{125}$I-IL-12 binding assays. Apparent dissociation constant ($K_D$) and binding sites per cell have been calculated by transformation of the data by the method of Scatchard.
[2]Steady state $^{125}$I-2-4E6 binding assays. Data transformed by the method of Scatchard.
[3]Human peripheral blood monomuclear cells (PBMC) were activated with PHA as described in the methods (PHA-PBMC).

EXAMPLE 15
MAb 2*4E6 Binding To Human Recombinant IL-12R Expressed in COS Cells The characteristics of the protein bound by mAb 2*4E6 fullfilled standard criterion for an IL-12R and therefore 2*4E6 was used in an expression cloning strategy to isolate a cDNA coding for the human IL-12R. A cDNA coding for the human IL-12R was isolated by this method (U. Gubler and A. O. Chua, unpublished observations). The IL-12R cDNA was engineered in a mammalian cell expression vector, transfected into COS-7 cells and the specificity for binding of $^{125}$I-IL-12 and $^{125}$I-2*4E6 was determined. Steady state binding of $^{125}$I-IL-12 to the rIL-12R expressing COS cells identifies a single binding site with an apparent affinity of 2–6 nM and approximately 150,000 sites/cell (FIGS. 10A and 10B). This low affinity IL-12 binding site corresponds to the low affinity site seen in the binding assays with human cells that naturally express IL-12R. The binding of $^{125}$I-2*4E6 to rIL-12R expressed in the COS cells is saturable and specific and identifies approximately 500,000 sites/cell (FIGS. 11A and 11B). COS cells transfected with an unrelated plasmid do not bind either $^{125}$I-IL-12 or $1^{25}$I-2*4E6 (data not shown). These data demonstrated unequivocally that mAb 2*4E6 was specific for the low affinity component of the IL-12R.

EXAMPLE 16
Analsis of mAb 2*4E6 Binding to IL-12R Positive Human Cells by Fluorescence Acitvated Cell Sorting (FACS)

The expression level of IL-12R on human cells could be regulated depending on the activation state of the cells, the cell cycle or the type of environment from which the cells are isolated. Previous data had demonstrated that PHA activation of PBMC leads to a gradual rise in IL-12R expression, reaching a maximum at 3–4 days after activation and decling thereafter. Desai et al., *J. Immunol.* Methods 148, 3125 (1992) To investigate the heterogeneity of IL-12R expression on PHA-activated PBMCs, Kit-225 and K6 cells, FACS analysis of IL-12R on these cells was determined with mAb 2*4E6 (FIGS. 12A, 12B and 12C). The fluorescence intensity of binding of 2*4E6 was specific and indicated that these three cell types expressed approximately equal numbers of IL-12R. Interestingly, the FACS analysis indicated that the cell population was fairly homogenous and did not have one population expressing no or low numbers of IL-12R and a second population that expressed very high numbers of IL-12R.

We claim:

1. An isolated immunoglobulin which binds selectively to a human IL-12 receptor said receptor having the amino acid sequence of SEQ ID No. 2.

2. An antiserum comprising the immunoglobin of claim 1.

3. The immunoglobulin of claim 2 which inhibits the binding of human IL-12 to the human IL-12 receptor and neutralizes human IL-12 bioactivity by binding to the human IL-12 receptor.

4. The immunoglobulin of claim 2 which binds to the human IL-12 receptor but does not inhibit the binding of human IL-12 to the human IL-12 receptor and does not neutralize human IL-12 bioactivity by binding to the human IL-12 receptor.

5. The immunoglobulin of claim 2 which is of murine origin.

6. The immunoglobulin of claim 1 which is a monoclonal antibody.

7. The immunoglobulin of claim 6 wherein said monoclonal antibody is in humanized form.

8. The immunoglobulin of claim 6 which is a single chain antibody.

9. A method for detecting the presence of cells expressing a human IL-12 receptor having the amino acid sequence of SEQ ID No. 2 comprising contacting a sample containing the cells with an immunoglobulin which specifically binds to said human IL-12 receptor so as to form a cellular complex between the human IL-12 receptor and the immunoglobulin; and detecting said cellular complex, detection of said cellular complex being indicative of the presence of cells which express said human IL-12 receptor.

10. The method of claim 9 wherein said immunoglobulin comprises a monoclonal antibody.

11. The method of claim 10 wherein the monoclonal antibody to the IL-12 receptor is covalently bound to a solid resin.

12. The method of claim 10 wherein said immunoglobulin is labeled with a detectable label.

13. The method of claim 12 wherein said detectable label is $^{125}$I.

14. An assay for detecting the presence of human IL-12 receptor having the amino acid sequence of SEQ ID No. 2 which comprises isolating cells from a subject; contacting a sample of said cells with a detectable immunoglobulin which selectively binds to said human IL-12 receptor; incubating said cells under conditions which allow the detectable immunoglobulin to bind to the human IL-12 receptor; and detecting the binding of said cells to said immunoglobulin, detection of the binding of said cells to said immunoglobulin being indicative of the presence of said human IL-12 receptor.

15. The assay of claim 14 wherein the said detectable is a monoclonal antibody.

16. The assay of claim 15 wherein the monoclonal antibody is labeled with $^{125}$I.

17. The assay of claim 15 wherein the binding is detected with $^{125}$I-labeled IL-12.

* * * * *